United States Patent

Dietz et al.

[11] Patent Number: 5,853,750
[45] Date of Patent: Dec. 29, 1998

[54] POLYMERIZED MICROEMULSION PRESSURE SENSITIVE ADHESIVE COMPOSITIONS AND METHODS OF PREPARING AND USING SAME

[75] Inventors: Timothy M. Dietz, St. Paul; Ying-Yuh Lu, Woodbury; Rosa Uy, St. Paul; Chung I. Young, Roseville, all of Minn.

[73] Assignee: Minnesota Mining and Manufacturing Company, St. Paul, Minn.

[21] Appl. No.: 935,385

[22] Filed: Sep. 23, 1997

Related U.S. Application Data

[60] Division of Ser. No. 507,006, Jul. 25, 1995, Pat. No. 5,670,557, which is a continuation-in-part of Ser. No. 188,269, Jan. 28, 1994, abandoned.

[51] Int. Cl.$^6$ .............................. A61F 13/02; B32B 7/12
[52] U.S. Cl. ......................... 424/448; 523/105; 523/111; 428/343; 428/354
[58] Field of Search .................... 523/105, 111; 424/448; 428/343

[56] References Cited

U.S. PATENT DOCUMENTS

| | | | |
|---|---|---|---|
| 3,890,292 | 6/1975 | Bohne et al. | 524/451 |
| 3,996,180 | 12/1976 | Kane | 260/29.6 H |
| 4,181,752 | 1/1980 | Martens et al. | 427/54.1 |
| 4,289,844 | 9/1981 | Sprecht et al. | 430/281 |
| 4,303,485 | 12/1981 | Levens | 204/159.24 |

(List continued on next page.)

FOREIGN PATENT DOCUMENTS

| | | |
|---|---|---|
| 0 391 343 A2 | 10/1990 | European Pat. Off. . |
| 0 430 517 A2 | 6/1991 | European Pat. Off. . |
| 0 531 005 A2 | 3/1993 | European Pat. Off. . |
| 2 197 791 | 6/1986 | United Kingdom . |
| WO 93/09713 | 5/1993 | WIPO . |
| WO 93/20165 | 10/1993 | WIPO . |

OTHER PUBLICATIONS

Candau et al., *Progr Colloid & Polymer Sci.*, 73:33–36 (1987).
Chew and Gan, *J. Polym. Sci.: Polym. Chem.*, 1985, 23, pp. 2225–2282.
Encyclopedia of Polymer Science Engineering; Wiley: New York 1987, vol. 9, p. 718.
Hague et al., Journal of Polymer Science: Part C: Polymer Letters, vol. 26, 429–432 (1988).
Kuo, et al., *Macromolecules*, 1987, 20, pp. 1216–1221.
Puig et al., *J. Colloid Interface Sci.*, 1990, vol. 137, pp. 308–310.
Puig et al., *Antec '91*, pp. 1145–1147.

(List continued on next page.)

*Primary Examiner*—Tae Yoon
*Attorney, Agent, or Firm*—Gary L. Griswold; John H Hornickel

[57] ABSTRACT

A polymerized microemulsion pressure sensitive adhesive composition is described. The composition has peel adhesion of at least 3 Newtons/100 mm as measured according to a PSTC-1 Test. The composition preferably has a bicontinuous structure of a continuous phase of a hydrophobic pressure sensitive adhesive polymer and a continuous phase of a hydrophilic polymer. The bulk properties of both polymers are retained in the bicontinuous structure. The composition is prepared from a microemulsion comprising a free-radically ethylenically unsaturated polar amphiphilic or hydrophilic monomer or oligomer in the aqueous phase, a free-radically ethylenically unsaturated hydrophobic monomer, having a glass transition temperature suitable for forming a pressure sensitive adhesive, in the oil phase, water, and surfactant. Uses for the pressure sensitive adhesive composition include biomedical articles, such as biomedical electrodes, medical skin coverings, and pharmaceutical delivery devices, and industrial articles, such as zinc/adhesive tapes used for cathodic protection of rebars embedded in concrete.

5 Claims, 6 Drawing Sheets

U.S. PATENT DOCUMENTS

| | | | |
|---|---|---|---|
| 4,338,232 | 7/1982 | Harris et al. | 523/414 |
| 4,442,258 | 4/1984 | Sunakawa et al. | 524/767 |
| 4,485,209 | 11/1984 | Fan et al. | 524/801 |
| 4,504,618 | 3/1985 | Irvine et al. | 524/457 |
| 4,521,317 | 6/1985 | Candau et al. | 252/8.55 D |
| 4,521,580 | 6/1985 | Turner et al. | 526/307.2 |
| 4,524,087 | 6/1985 | Engel | 427/2 |
| 4,539,996 | 9/1985 | Engel | 128/640 |
| 4,554,924 | 11/1985 | Engel | 128/640 |
| 4,564,664 | 1/1986 | Chang et al. | 524/833 |
| 4,616,057 | 10/1986 | Lindemann et al. | 524/458 |
| 4,681,912 | 7/1987 | Durand et al. | 524/827 |
| 4,715,382 | 12/1987 | Strand | 128/640 |
| 4,739,008 | 4/1988 | Robinson et al. | 524/801 |
| 4,742,086 | 5/1988 | Masamizu et al. | 521/62 |
| 4,745,154 | 5/1988 | Ruffner | 524/801 |
| 4,846,185 | 7/1989 | Carim | 128/614 |
| 4,848,353 | 7/1989 | Engel | 128/640 |
| 4,851,216 | 7/1989 | Lee | 424/78 |
| 4,931,282 | 6/1990 | Asmus et al. | 424/448 |
| 4,939,190 | 7/1990 | Tomioka et al. | 523/206 |
| 4,952,650 | 8/1990 | Young et al. | 524/194 |
| 5,012,810 | 5/1991 | Strand et al. | 128/640 |
| 5,049,275 | 9/1991 | Gillberg-LaForce et al. | 210/500.27 |
| 5,133,356 | 7/1992 | Bryan et al. | 128/640 |
| 5,151,217 | 9/1992 | Price | 252/312 |
| 5,190,997 | 3/1993 | Lindemann et al. | 524/458 |
| 5,238,992 | 8/1993 | Outubuddin | 524/710 |
| 5,264,278 | 11/1993 | Mazurek et al. | 428/317.3 |
| 5,270,358 | 12/1993 | Asmus | 524/55 |
| 5,276,079 | 1/1994 | Duan et al. | 524/386 |
| 5,382,451 | 1/1995 | Johnson et al. | 427/208.4 |
| 5,416,134 | 5/1995 | Skoglund | 523/201 |
| 5,505,200 | 4/1996 | Takaki | 128/640 |
| 5,506,059 | 4/1996 | Robbins et al. | 428/457 |
| 5,521,229 | 5/1996 | Lu et al. | 522/40 |
| 5,624,973 | 4/1997 | Lu et al. | 522/40 |
| 5,650,060 | 7/1997 | Huang et al. | 205/730 |

OTHER PUBLICATIONS

Outubuddin et al., "Preparation and Characterization of Porous Polymers from Microemulsions" in Chapter 5 of ACS Symposium Series 384, Polymer Association Structures, American Chemical Society, 1989.

Raj et al., *Langmuir*, 1991, vol. 7, pp. 1378 ff. and 2586 ff.

Sasthav et al., *Langmujir*, 7, 1378–1382 (1991).

Stoffer and Bone, *J. Dispersion Sci. Technol.*, 1980, 1, pp. 37–54.

Vaškovaá et al., *Makromol. Chem*, 192, 1339–1347 (1991).

PSTC–1, Peel Adhesion for Single Coated Tapes 180° Angle (with Appendages A, B, C, and D), Pressure Sensitive Tape Council, Nov. 1975.

Vašková et al., *Makromol. Chem*, 192, 989–997 (1991).

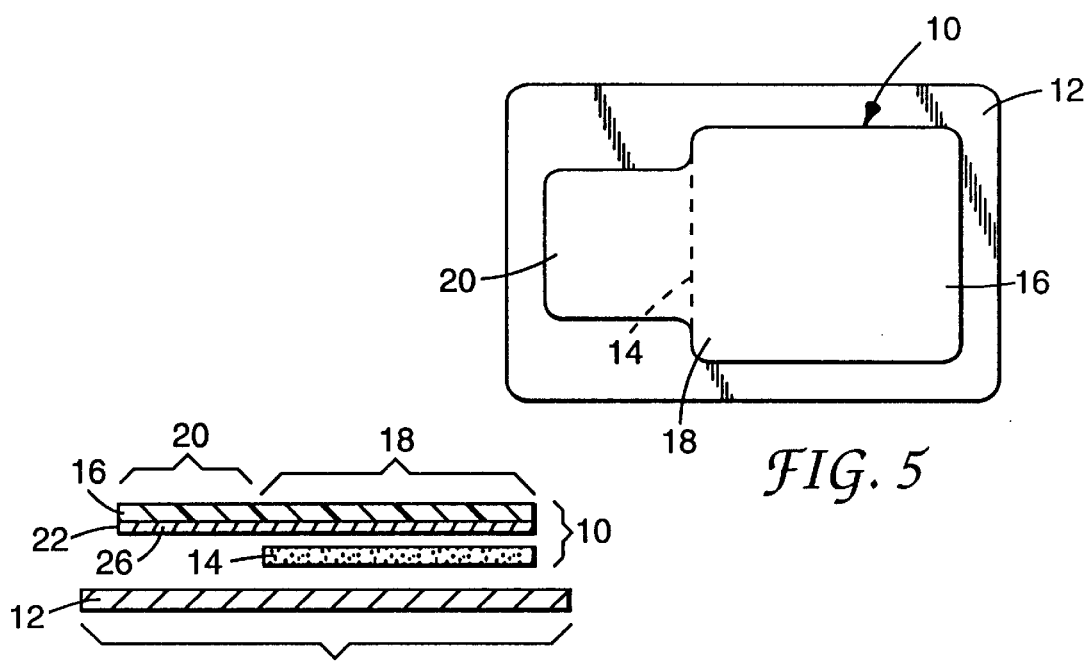
FIG. 5
FIG. 6
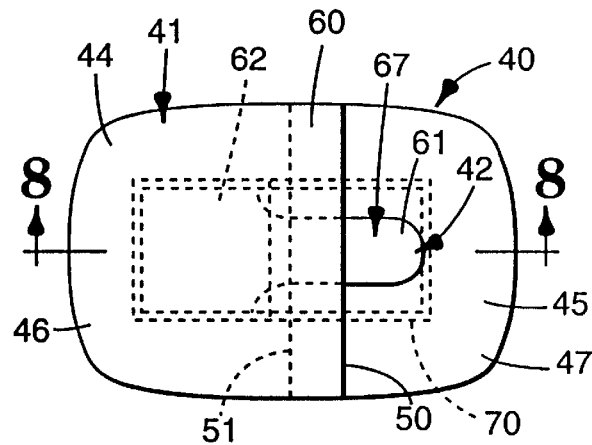
FIG. 7
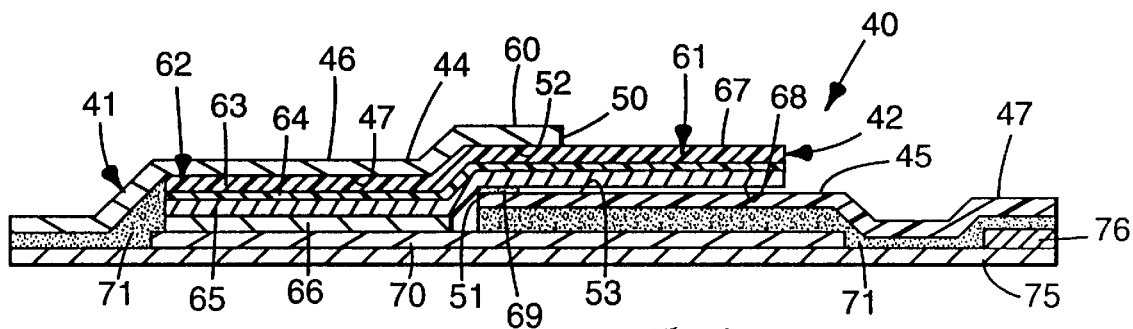
FIG. 8

POLYMERIZED MICROEMULSION PRESSURE SENSITIVE ADHESIVE COMPOSITIONS AND METHODS OF PREPARING AND USING SAME

CROSS REFERENCE TO RELATED APPLICATION

This is a division of application Ser. No. 08/507,006 filed Jul. 25, 1995, now U.S. Pat. No. 5,670,557 which is a continuation-in-part of prior application Ser. No. 08/188,269, filed on Jan. 28, 1994 now abandoned.

FIELD OF THE INVENTION

This invention relates to pressure sensitive adhesive compositions and methods of preparing and using such compositions.

BACKGROUND OF THE INVENTION

Microemulsions are water-oil colloidal dispersions stabilized by an appropriate mixture of surface-active agents (usually a surfactant such as a soap and a cosurfactant such as a short chain alcohol). By contrast with conventional milky emulsions, for which the stability is of purely kinetic origin, microemulsions are thermodynamically stable and form spontaneously at contact. The small size of the spherical droplets (about 10 nm) dispersed in the continuous medium explains their optical transparency (*Encyclopedia of Polymer Science Engineering*; Wiley: New York 1987, Vol. 9, p. 718, incorporated by reference herein).

Microemulsions differ from macroemulsions and miniemulsions. Macroemulsions, conventionally known as emulsions, are thermodynamically unstable mixtures of two immiscible liquids, one of which is dispersed in the form of fine droplets having diameters greater than 100 nm in the other liquid. Macroemulsions are turbid, usually milky white in color. Miniemulsions are opaque, thermodynamically unstable emulsions containing two immiscible fluids which are prepared using a mixture of ionic surfactant and a cosurfactant such as a long chain fatty-alcohol or n-alkane. Relatively high mechanical shear is required to produce miniemulsions with an average droplet size of 100 to 500 nm.

Microemulsions can be oil-in-water (water-continuous) types, water-in-oil (oil-continuous) types and bicontinuous types. In bicontinuous microemulsions both the oil and water phases coexist in interconnected continuous domains with surfactant molecules located at the interface. The water, oil, and cosurfactant (usually a short chain alcohol) in bicontinuous microemulsion systems diffuse at rates that are comparable to those of the neat components.

In principle, free-radical polymerization of a vinyl monomer can be achieved in either the continuous phase or the dispersed phase of oil-in-water (o/w), water-in-oil (w/o), or bicontinuous microemulsions. Kuo, et al. (*Macromolecules*, 1987, 20, p. 1216) describe polymerization of styrene in the dispersed phase of an o/w microemulsion, while Candau et al. (U.S. Pat. No. 4,681,912) have disclosed polymerization of water-soluble monomers in the dispersed phase of w/o microemulsions. Chew and Gan (*J. Polym. Sci.: Polym. Chem.*, 1985, 23, p. 2225) attempted to polymerize methyl methacrylate as the continuous phase of a w/o emulsion with water dispersed in the polymer matrix. However, no evidence of a bicontinuous structure of the resultant polymer was observed. Stoffer and Bone (*J. Dispersion Sci. Technol.*, 1980, 1, p. 37) also report the polymerization of methyl methacrylate as the continuous phase in a system which also contained sodium dodecylsulfonate, pentanol and water.

Shah et al., (European Patent Application 391,343) disclose polymerization of, e.g., acrylate monomers, as the dispersed phase of aqueous microemulsions, to produce extremely small polymeric particles.

Puig et al. (*J. Colloid Interface Sci.*, 1990, Vol. 137, p. 308) discuss polymerization of acrylic acid/styrene microemulsions wherein one of the monomers (acrylic acid) is significantly soluble in the water phase. The resultant copolymer consists of isolated acrylic acid units randomly distributed among polystyrene blocks.

The above references teach only thermal methods of initiating polymerization. None of the references discloses the preparation of a polymer having a bicontinuous structure wherein both phases are solids, or a bicontinuous polymer in which hydrophobic and hydrophilic polymers coexist in both phases and which arises from polymerization of a microemulsion. Further, none of the above references teach the formation of a pressure sensitive adhesive composition from a microemulsion.

Price (U.S. Pat. No. 5,151,217) has disclosed the preparation of bicontinuous microemulsions of hydrophobic monomers such as styrene, alkyl esters of (meth)acrylates, plus a crosslinking agent, in the presence of a unique addition-polymerizable cationic surfactant. The objective of Price was to prepare, via photopolymerization, solid polymers which could be used in separation processes. The preparation or polymerization of a microemulsion in which free-radically polymerizable monomers are present in both the water and oil phases is not disclosed, nor is the use of a polar monomer in either phase disclosed. Finally, the product polymers exhibit a solid phase and a liquid phase rather than two solid phases. No preparation of a polymerized microemulsion pressure sensitive adhesive composition is disclosed.

Photopolymerization of bicontinuous microemulsions has been reported by Cheung et al. (*Langmuir*, 1991, Vol. 7, pp. 1378 ff. and 2586 ff.). Styrene/water microemulsions produced porous polystyrene membranes. Polymerizations of methyl methacrylate/acrylic acid microemulsions both in the presence and absence of added surfactant produced porous polymeric solids reported to have good mechanical stability. Although a polar monomer is reportedly employed in these systems, microscopic examination showed that the resulting copolymeric materials were single-phased porous systems.

European Patent Publication 0 432 517, assigned to the assignee of the present invention and incorporated by reference herein, describes photopolymerization of the hydrophobic phase of bicontinuous microemulsions which also contain biologically active materials, to form a porous membrane, film, or bead. Polymerization of monomers in the hydrophilic phase is not disclosed or claimed. No preparation of a polymerized microemulsion pressure sensitive adhesive composition is disclosed.

U.S. Pat. No. 5,238,992 (Outubuddin) discloses microemulsion polymer blends and composites having controlled porosity prepared from microemulsions containing both hydrophilic and hydrophobic phases. The microemulsions are prepared with surfactant systems, optional co-solvents, and hydrophilic monomer(s) in the hydrophilic phase and hydrophobic monomer(s) in the hydrophobic phase. The resulting blend shows pores in both micron and submicron regions, and normally displays greater porosity when the microemulsion is of the bicontinuous type in contrast to either oil-in-water type or the water-in-oil type. No preparation of a polymerized microemulsion pressure sensitive adhesive composition is disclosed.

U.S. Pat. No. 5,270,358 (Asmus) discloses a two-phase composite having a continuous phase of hydrophobic pressure sensitive adhesive and a dispersed phase of hydrogel that can also have pressure sensitive adhesive properties. Discrete particles of hydrogel do not provide a continuous phase of the hydrophilic phase of the composite. No preparation of polymerized microemulsion pressure sensitive adhesive composition is disclosed.

PCT Publication WO 93/09713 (Dietz et al.) discloses a two-phase composite of ionically-conductive pressure sensitive adhesive having a continuous phase of hydrophilic, solid state pressure-sensitive adhesive that is ionically conductive regardless of an amount of water present in the composition and a discontinuous phase of domains of hydrophobic, pressure-sensitive adhesive composition present in the continuous phase in an amount to enhance pressure-sensitive adhesive properties for contacting mammalian skin while maintaining acceptable alternating current impedance. No preparation of a polymerized microemulsion pressure sensitive adhesive is disclosed.

SUMMARY OF THE INVENTION

The art has not recognized the ability to produce nor the need for pressure sensitive adhesive compositions prepared from the polymerization of microemulsions.

Microemulsions have been used to produce porous polymers but have not been used to yield polymers having peel adhesion pressure sensitive adhesive properties.

The use of the phrase "peel adhesion" pressure sensitive adhesive properties with respect to this invention is based on a specific test established by the Pressure Sensitive Adhesive Tape Council of Chicago, Ill. ("PSTC"): namely, PSTC-1 (11/75) entitled "Peel Adhesion for Single Coated Tapes 180° Angle", ("PSTC-1 Test") the disclosure of which is incorporated by reference herein. This PSTC-1 Test determines peel adhesion as the force required to remove a pressure sensitive adhesive tape from a panel or its own backing at a specified angle and speed.

The present invention broadly is a polymerized microemulsion pressure sensitive adhesive composition having peel adhesion of at least 3 Newtons/100 mm according to the PSTC-1 Test (hereafter abbreviated "polymerized microemulsion PSA").

Using PSTC-1 Test, polymers having pressure sensitive adhesive properties of at least 3 Newtons/100 mm qualify as a polymerized microemulsion PSA of the present invention. Any polymer having less than 3 Newtons/100 mm 180° peel adhesion has insufficient adhesiveness to qualify as a pressure sensitive adhesive for purposes of this invention. Below 3 Newtons/100 mm, the adhesive is so weak that it is not reliable for consistent, planned usage.

Preferably, a polymerized microemulsion PSA has the advantage over the two-phase (continuous-discontinuous) composites in the art of providing a composition that exhibits both hydrophobic and hydrophilic properties consistent with both a continuous hydrophobic phase and a continuous hydrophilic phase. The continuous hydrophobic phase provides excellent hydrophobic pressure sensitive adhesive properties and can provide delivery of pharmaceutically active agents; the continuous hydrophilic phase provides excellent hydrophilic pathways for ionic conductivity, moisture vapor transmission, and delivery of pharmaceutically active agents.

Polymerized microemulsion PSA's of the present invention solve a problem insufficiently resolved by U.S. Pat. No. 5,270,358 by providing a continuous hydrophilic phase for ionic conductivity through the bulk of the composition, regardless of the thickness of the composition. Polymerized microemulsion PSA's of the present invention are ionically conductive; composites disclosed in U.S. Pat. No. 5,270,358 are not because the discrete gel particles are the dispersed phase.

Polymerized microemulsion PSA's of the present invention solve a problem insufficiently resolved by PCT Publication WO 93/09713 by providing a continuous hydrophobic phase for excellent long-term hydrophobic pressure sensitive adhesiveness that is desired for certain biomedical applications such as monitoring biomedical electrodes, wound dressings, and other multiple-day procedures or treatments. Polymerized microemulsion PSA's of the present invention have continuing adhesion to mammalian skin for at least three days; two-phase composites disclosed in PCT Publication WO 93/09713 do not maintain adhesion to mammalian skin for more than about one day.

Polymerized microemulsion PSA's of the present invention are not merely aggregated double phases of separable regions of hydrophobicity and hydrophilicity. Polymerized microemulsion PSA's of the present invention provide structural integrity throughout both continuous phases. Because neither phase is a dispersed phase, neither phase is separable from the other phase. For example, polymerized microemulsion PSA's of the present invention can maintain structural integrity in the presence of solvents of either the continuous hydrophilic polymer or the continuous hydrophobic polymer.

While not being limited to a particular theory, polymerized microemulsion PSA's of the present invention preferably have both a hydrophobic continuous phase and a hydrophilic continuous phase because of the formation of the morphology during polymerization of the microemulsion. The hydrophobic continuous phase is formed as hydrophobic monomers polymerize; the hydrophilic continuous phase is formed as hydrophilic or amphiphilic monomers or oligomers polymerize. The resulting polymerized microemulsion composition has both continuous hydrophobic and continuous hydrophilic properties, such that solvents of neither the hydrophobic polymer nor solvents of the hydrophilic polymer can dissolve the resulting polymerized microemulsion composition.

It presently is not known whether there are independent hydrophobic and hydrophilic polymers so intertwined at the time of polymerization so as to form a mechanical integrity that resists solvation or whether there is some copolymerization of hydrophobic monomers and hydrophilic monomers so as to form a chemically covalent integrity at some regions where hydrophobic monomers and hydrophilic monomers have copolymerized.

But the morphology of the polymerized microemulsion PSA's is different than a two-phase composite where one phase is dispersed and the other phase is continuous, even if the exact morphology can not be described on a molecular level, because the composition of the present invention exhibits bulk properties that are consistent with continuity of both a hydrophobic polymeric phase and with continuity of a hydrophilic polymeric phase.

"Bicontinuous structure" has been chosen to describe the morphology of the polymerized microemulsion that exhibits properties consistent with both a hydrophobic continuous phase and a hydrophilic continuous phase.

Polymerized microemulsion PSA's of the present invention preferably provide the optimum bicontinuous structure not previously known in the art: both a continuous hydrophobic phase and a continuous hydrophilic phase.

Polymerized microemulsion PSA's are derived from concurrent polymerization of a free-radically polymerizable hydrophilic or amphiphilic monomer or oligomer in the aqueous (water) phase of a microemulsion and a concurrent polymerization of a free-radically polymerizable hydrophobic monomer in the organic (oil) phase to form a PSA. Preferably, the PSA has a bicontinuous structure and even more preferably has two solid, substantially nonporous bicontinuous phases. In any event for the present invention, the choice of hydrophobic monomers and the choice of weight percents used to form the polymer are selected to optimize pressure sensitive adhesive properties of the resulting composition.

A preferred polymerized microemulsion PSA of the present invention with a substantially nonporous, bicontinuous structure would find utility especially in applications where the bulk properties of both hydrophilic polymers and hydrophobic polymers PSA's are required simultaneously.

As used herein, the term "substantially nonporous" means that pores or open spaces in the composite do not exist on a level greater than 0.1 µm diameter. "Substantially nonporous" is specifically distinguished from a porous structure on a micrometer level as disclosed in U.S. Pat. No. 5,238,992 and Qutubuddin et al., "Preparation and Characterization of Porous Polymers from Microemulsions" in Chapter 5 of ACS Symposium Series 384, Polymer Association Structures, American Chemical Society, 1989.

Thus, the present invention departs from the art by providing a polymerized microemulsion PSA. Preferably, the PSA has a bicontinuous structure. The polymerized microemulsion PSA is prepared from a microemulsion where monomers are selected so as to provide a resulting pressure sensitive adhesive.

Preferably, the polymerized microemulsion PSA is a solid, substantially nonporous bicontinuous polymeric material having pressure sensitive adhesive properties.

The present invention also departs from the art by providing a method of preparing the polymerized microemulsion PSA by careful, controlled selection of monomers or oligomers, surfactants, and water to form a microemulsion that, when subjected to free-radical polymerization, yields a PSA, preferably a PSA having a bicontinuous structure.

The pressure sensitive adhesive composition of the invention comprises:

a pressure sensitive adhesive polymerization product of a microemulsion having an aqueous phase and an oil phase, the microemulsion comprising:
(a) about 2 to about 60 weight percent water;
(b) about 2 to about 90 weight percent free-radically copolymerizable ethylenically-unsaturated amphiphilic or hydrophilic monomer or oligomer;
(c) about 5 to about 85 weight percent hydrophobic free-radically copolymerizable ethylenically-unsaturated monomer suitable for forming a hydrophobic polymer having a glass transition temperature contributed by the hydrophobic monomer to provide the hydrophobic polymer to have pressure sensitive adhesive properties;
(d) about 2 to about 70 weight percent of a surfactant selected from the group consisting of (i) nonionic surfactants, cationic surfactants, anionic surfactants, and mixtures thereof, wherein said surfactants are not copolymerizable with the species of element (b) and the monomer of element (c), (ii) ethylenically-unsaturated nonionic surfactants, cationic surfactants, anionic surfactants, and mixtures thereof which are copolymerizable with the species of element (b) and monomer of element (c), (iii) both (i) and (ii);

wherein said percentages of (a), (b), (c), and (d) are each based upon the total weight of the microemulsion; and
(e) about 0.005 to about 5 parts by weight of a lipophilic photoinitiator, wherein the amount of the photoinitiator is based on the total weight of elements (a) plus (b) plus (c) plus (d).

Preferably, the polymerization product has a bicontinuous structure that at least the hydrophobic continuous phase is a pressure sensitive adhesive.

Preferably, the hydrophobic continuous phase is ionically conductive. Preferably, the hydrophilic continuous phase also has pressure sensitive adhesiveness.

Preferably, both hydrophobic continuous phase and hydrophilic continuous phase are substantially nonporous solids.

The polymerized microemulsion PSA's of this invention are the result of concurrent polymerization of free-radically polymerizable species in both the aqueous phase and organic phase of a microemulsion. Preferably, at the time of concurrent polymerization in each phase, the aqueous phase and the organic phase coexist in interconnected continuous domains; they are a bicontinuous structure.

Thus, polymerization in the aqueous phase results in hydrophilic polymeric domains having hydrophilic bulk properties, while polymerization in the oil phase results in hydrophobic polymeric domains having hydrophobic bulk properties. Because the concurrent polymerization occurs, a composition results, preferably a bicontinuous structure, that can resist solvation by solvents that solvate the hydrophobic polymer or by solvents that solvate the hydrophilic polymer.

There are four essential components to the microemulsions used in the present invention: (1) water to form the aqueous phase; (2) hydrophobic monomers comprising the oil phase and capable of forming a hydrophobic polymer having pressure sensitive adhesive properties; (3) hydrophilic or amphiphilic monomers or oligomers residing at least partially in the water and capable of forming a hydrophilic polymer; and (4) surfactant to construct the microemulsion. Control over the selection of the types of monomers or oligomers and control over the weight percents of the components permits the formation of microemulsions that result in polymerized microemulsion PSA's, preferably those having a bicontinuous structure.

The aqueous phase comprises water and at least one free-radically copolymerizable ethylenically-unsaturated polar, amphiphilic or hydrophilic monomer or oligomer. The aqueous phase can optionally further comprise one or more of the components selected from the group consisting of a non-reactive polar oligomeric additive; a free-radically polymerizable, photochemically-activated crosslinker; a cosolvent; a water-soluble free-radical photopolymerization initiator; a water-soluble free-radical thermal initiator, a water-soluble additive such as those selected from the group consisting of plasticizers, electrolytes, dyes, and pharmaceutically-active materials.

As used herein, the term "polar" refers to species which exhibit a measurable dipole moment.

As used herein, the term "oligomer" refers to polymeric species having at least two and up to about 2000 repeating units.

As used herein, the term "amphiphilic" refers to species which contains both polar water-soluble and hydrophobic water-insoluble groups.

The organic phase comprises at least one free-radically polymerizable ethylenically-unsaturated hydrophobic monomer that is suitable for forming a hydrophobic polymer having a glass transition temperature (Tg) having pressure sensitive adhesive properties, a free-radically polymerizable ethylenically-unsaturated polar monomer, and an oil-soluble free-radical photopolymerization initiator. The organic phase can optionally further comprise one or more of the components selected from the group consisting of a nonreactive polar oligomeric additive; an oil soluble crosslinking agent which can contribute to the bulk properties of the resulting composition; an oil soluble chain-transfer agent; an oil-soluble free-radical thermal initiator; oil-soluble functional additives such as those selected from the group consisting of plasticizing agents, dyes, pharmaceutically-active materials, and tackifiers.

The surfactant component of the microemulsion is a compatible surfactant, which can be nonionic or ionic (i.e., anionic or cationic), preferably, anionic or nonionic. Where appropriate, one can include additives and fillers (such as a web, a scrim or silica or activated carbon black or fibrous fillers), which are soluble in neither the aqueous phase nor the organic phase but which may be disposed within the final composition, preferably having a substantially nonporous, bicontinuous structure.

Transparent microemulsions form spontaneously on admixture of the components which make up the aqueous phase, the organic phase, and the surfactant in any order. One method of the present invention preferably mixes the components in a regular order to define and achieve reproducible microemulsions. The microemulsion is then cast into an appropriate mold and irradiated with ultra-violet light to effect free-radical polymerization, or it is coated onto a substrate and irradiated with ultraviolet light to effect free-radical polymerization on the substrate, or it can be cast so as to encompass a sheet or mesh of reinforcing material, such as a scrim, etc., then irradiated to effect free-radical polymerization.

Preferably, the order of mixing is as follows:

(1) if any combination of hydrophilic monomer(s) and/or amphiphilic monomer(s) are desired, they are mixed together in a weight percent ratio of from about 0/100 to about 100/0 to form a first mixture;

(2) the hydrophobic monomer(s) are mixed into the first mixture in a weight percent ratio of from about 10/90 to about 80/20 hydrophobic monomers/first mixture to form a second mixture;

(3) the surfactant(s) are mixed into the second mixture in a weight percent ratio of from about 5/95 to about 40/60 surfactant/second mixture to form a third mixture;

(4) the initiator(s) are mixed into the third mixture in a weight percent ratio of from about 0.01/99.99 to about 2/98 initiator/third mixture to form a fourth mixture;

(5) independently, the water and optionally, any water-soluble or water-dispersible additives are mixed together in a weight percent ratio of from about 100/0 to about 80/20 to form an aqueous mixture; and (6) the aqueous mixture and fourth mixture are mixed together in a weight percent ratio of from about 5/95 to about 50/50 aqueous mixture/fourth mixture to form a microemulsion.

A feature of the present invention is that the bulk properties of the hydrophilic polymer (polymerized in the aqueous phase of the microemulsion) coexist in continuous domains with the bulk properties of the hydrophobic polymer PSA (polymerized in the oil phase of the microemulsion).

Another feature of the present invention is that the polymerized microemulsion PSA of the present invention can bring the bulk properties of the hydrophilic polymer as an improvement to a conventional hydrophobic polymer PSA and vice versa.

An advantage of the present invention is that neither phase of the polymerized microemulsion PSA is a dispersed phase, isolated from continuity in the composition, thereby providing a continuous phase of pressure sensitive adhesive properties and a continuous phase of hydrophilic polymer properties, such as moisture vapor transmission or ionic conductivity, or both.

Another advantage of the present invention is that choice of oligomers from which to polymerize the hydrophilic polymer results in preferred substantially nonporous polymerized microemulsion PSA's.

Another advantage of the present invention is that choice of monomers or oligomers from which to polymerize the hydrophilic polymer results in a hydrophilic PSA, preferably in a bicontinuous structure with the hydrophobic PSA, providing two different types of pressure sensitive adhesive properties that can be useful in situations where different pressure sensitive adhesive properties are required due to changing conditions such as perspiration or body exudate contacting the polymerized microemulsion PSA after initial adhesion and placement. It is possible using the present invention to provide both a "dry stick" performance and a "wet stick" performance for a health care application involving contacting mammalian skin.

Another advantage of the present invention is that merger of pressure sensitive adhesive bulk properties and a hydrophilic polymer bulk properties into a single polymerized microemulsion PSA merges applicability in health care usage. It is possible using the present invention to provide both a biocompatible, hydrophobic skin pressure sensitive adhesive of longer term adhesive duration and an ionically conductive pressure sensitive adhesive of shorter term adhesive duration. In the case of biomedical electrodes, the necessity for some electrodes to provide longer term adhesion via a border area of a biocompatible hydrophobic skin pressure sensitive adhesive can be eliminated by use of a polymerized microemulsion PSA of the present invention. The elimination of one electrode component saves surface area of the electrode for other uses, reduces the surface area of the electrode for better patient interaction, and can reduce expense in construction of the electrode.

BRIEF DESCRIPTION OF THE DRAWINGS

Each combination of phases of a microemulsion requires a specific formulation. The phase diagrams of FIGS. 2–4 indicate useful ranges of concentration for major components of the microemulsions in accordance with this invention, at a given identified surfactant weight percent.

FIG. 5 is a top plan view of a biomedical electrode containing a polymerized microemulsion PSA of the present invention, used for diagnosis or monitoring of heart conditions of a mammalian patient.

FIG. 6 is a cross-sectional view of the biomedical electrode of FIG. 5.

FIG. 7 is a top plan view of a monitoring biomedical electrode containing a polymerized microemulsion PSA of the present invention, used for longer term diagnosis or monitoring of heart conditions.

FIG. 8 is a cross-sectional view of the monitoring biomedical electrode of FIG. 7.

EMBODIMENTS OF THE INVENTION

Figure 1:
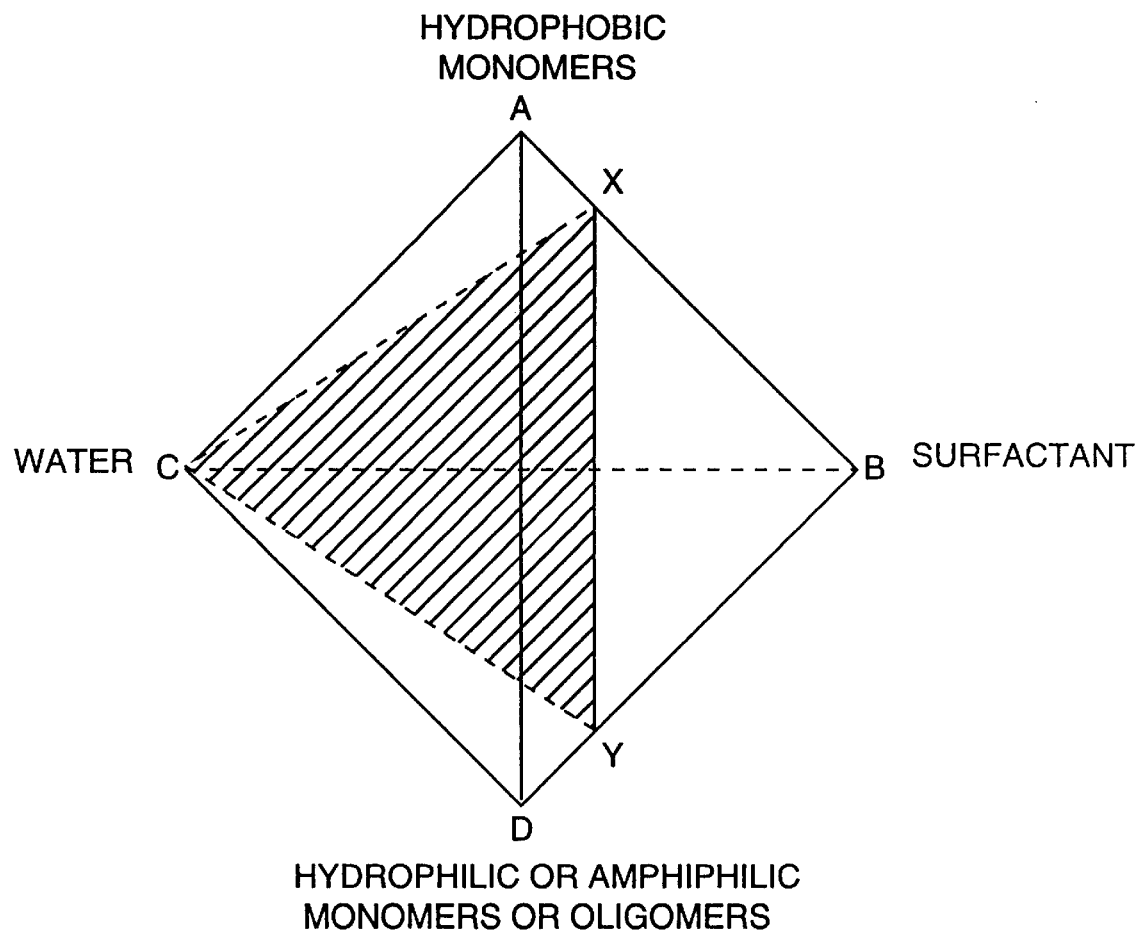
FIG. 1 is a four component diagram that demonstrates the variability possible for each of the four components used in forming microemulsions of the present invention, and including a triangular slice described below representing the three component diagrams of FIGS. 2–4 below.

Polymerized microemulsions that are not pressure sensitive adhesive can be prepared using many of the following components. Copending, coassigned U.S. patent application Ser. No. 08/189,060 (Lu et al.) discloses such polymer composites, the disclosure of which is incorporated by reference herein. The polymerized microemulsions of the present invention employ hydrophobic monomers suitable for forming a hydrophobic polymer having pressure sensitive adhesive properties according to the PSTC-1 Test described above. Also, microemulsions for forming polymerized microemulsion PSA's can have different final weight percents in the PSA, according to the scope of the present invention. Also, microemulsions for forming polymerized microemulsion PSA's can require evaporation of some water content of the resulting polymer in order to form a pressure sensitive adhesive.

I. Aqueous Phase

Prior to polymerization commencing, the aqueous phase of the microemulsion comprises water, free radically (co) polymerizable ethylenically unsaturated polar hydrophilic or amphiphilic monomer(s) or oligomer(s), optional water soluble initiator, and optional water soluble additive.

I.a. Water

The microemulsion of the present invention comprises from about 2 to about 50 percent by weight of water, preferably about 5 to about 30 percent by weight, and, most preferably about 6 to about 25 percent by weight, based upon the total weight of the microemulsion. Preferably the microemulsion comprises deionized water. Preferably, water also includes water soluble additives selected for properties of the PSA in ultimate usage. To determine the most appropriate weight percent of water to be included in the microemulsion, as stated above, the water is added incrementally until a clear microemulsion region is reached. This titration of water, repeated for various mixtures of other components of the proposed microemulsion, is represented by a three component diagram shown in FIGS. 2–4 with surfactant being fixed at a given weight percent in the various mixtures prior to titration with water.

I.b. Free-Radically (Co)Polymerizable Ethylenically-Unsaturated Polar Species

The aqueous phase of the present invention comprises at least one free-radically polymerizable ethylenically-unsaturated polar monomer or oligomer. The polar monomers or oligomers can be oil insoluble (hydrophilic) or can be both water soluble and oil soluble (amphiphilic). Preferably, use of polar oligomers in the aqueous phase promotes formation of a substantially nonporous bicontinuous structure for the polymerized microemulsion PSA of the present invention.

Monomers are selected from the group consisting of polar monomers which are substantially insoluble in the oil phase and polar monomers other than oil-insoluble monomers (i.e. polar monomers which are both water soluble and oil soluble).

The microemulsion cumulatively comprises from about 2 to about 90 percent by weight of the required hydrophilic or amphiphilic monomers or oligomers preferably from about 5 to about 70 percent by weight, and most preferably from about 10 to about 60 weight percent, based upon the total weight of the microemulsion, depending upon the desired properties of the polymerized microemulsion PSA.

I.b.i. Polar Ethylenically-Unsaturated Free-Radically (Co)Polymerizable Oligomers Useful polar ethylenically-unsaturated free-radically (co) polymerizable oligomers which are substantially insoluble in the oil phase or which are both water soluble and oil soluble include but are not limited to those selected from the group consisting of polyethylene oxide acrylates, polyethylene oxide diacrylates, polyethylene glycol acrylates, polyethylene glycol diacrylates, polyurethane acrylates, polyurethane diacrylates, N-vinylpyrrolidone macromer, and mixtures thereof. The polyethylene oxide acrylates and diacrylates are preferred. The most preferred oligomer comprises polyethylene oxide acrylate because of availability and ease of formulation. Useful oligomers typically have a number average molecular weight of about 100 to about 100,000, preferably about 100 to about 60,000, and most preferably about 100 to about 5000 for optimal physical properties (e.g., water absorption, nonporosity, strength) of the polymer composite preferably having a substantially nonporous, bicontinuous structure.

I.b.ii. Substantially Oil-Insoluble Free-Radically (Co) Polymerizable Ethylenically-Unsaturated Polar Monomers A first type of optional polar monomer is a water-soluble free-radically (co)polymerizable ethylenically-unsaturated polar monomer that is substantially insoluble in the oil phase. "Substantially oil-insoluble" and "water-soluble" both mean that the monomer has a solubility of less than about 0.5% by weight in the oil phase and exhibits a distribution ratio at a given temperature (preferably about 25° to 35° C.) of concentration in the oil phase to concentration in the aqueous phase of less than about 0.005. Such monomer may be nonionic, e.g., acrylamide, or may be ionic. Mixtures of nonionic and ionic monomers may be used. Ionic monomers conforming to these criteria include but are not limited to those selected from the group consisting of sodium styrene sulfonate, potassium acrylate, sodium acrylate, sodium methacrylate, ammonium acrylate, sodium 2-acrylamido-2-methylpropane sulfonate, 4,4,9-trimethyl-4-azonia-7-oxa-dec-9-ene-1-sulfonate, N,N- dimethyl-N-(beta-methacryloxyethyl)ammonium propionate betaine, trimethylamine methacrylamide, 1,1-dimethyl-1-(2,3-dihydroxypropyl)amine methacrylamide, and other zwitterionic ethylenically-unsaturated monomers having the requisite solubility requirements, mixtures thereof, and the like. Preferred oil-insoluble polar monomers include those selected from the group consisting of acrylamide, sodium styrene sulfonate, sodium acrylate, sodium 2-acyrlamido-2-methylpropane sulfonate, sodium methacrylate, and mixtures thereof, due to ease of formulation and desirable properties when polymerized.

I.b.iii. Free-Radically (Co)Polymerizable Ethylenically-Unsaturated Polar Monomers Other Than I.b.ii.

Many polar monomers known in the art exhibit some solubility in both water and oil. They can have a solubility of about 0.5% or greater in the oil phase and exhibit a distribution ratio at a given temperature (preferably about 25° C. to 30° C.) of concentration in the oil phase to a concentration in the aqueous phase of greater than or equal to about 0.005. Useful polar ethylenically-unsaturated free-radically (co)polymerizable monomers partitionable between the aqueous phase and the oil phase of the microemulsion of this invention include but are not limited to those selected from the group consisting of N-vinylpyrrolidone, N-vinylcaprolactam, (meth)acrylic acid, hydroxyethyl (meth)acrylate, itaconic acid, styrene sulfonic acid, N-substituted acrylamides, N,N-disubstituted acrylamides, N,N-dimethylaminoethyl methacrylate, 2-acrylamido-2-methyl propane sulfonic acid, and mixtures thereof. Preferred polar partitionable monomers include those selected from the group consisting of (meth)acrylic acid, N-vinylpyrrolidone, N-vinylcaprolactam, N,N-dimethylaminoethyl methacrylate, N,N-dimethylacrylamide, styrene sulfonic acid, 2-acrylamido-2-methyl propane sulfonic acid, and mixtures thereof. Most-preferred polar partitionable monomers include those selected from the group consisting of acrylic acid, N-vinylpyrrolidone, N-vinylcaprolactam, N,N-dimethylacrylamide, and mixtures thereof, because of the favorable properties, such as physical strength, they can impart to the biphasic polymer composite.

I.c. Water-Soluble Initiators

The aqueous phase may optionally further comprise a water-soluble free-radical polymerization initiator selected from the group consisting of thermal initiators, photoinitiators, and mixtures thereof.

I.c.i. Water-Soluble Photoinitators

Water-soluble photoinitiators useful in the present invention are photoinitiators which generate free radicals on exposure to electromagnetic (usually ultraviolet) radiation which act as initiators for the (co)polymerization of the hydrophilic monomer(s), the oleophilic monomer(s), the (co)polymerizable oligomers, and, when present, the (co)polymerizable surfactant as detailed below. Useful water-soluble photoinitiators include but are not limited to those selected from the group consisting of benzophenones substituted with an ionic moiety, a hydrophilic moiety or both; thioxanthones substituted with an ionic moiety, a hydrophilic moiety or both, and 4-substituted-(2-hydroxy-2-propyl)phenyl ketones, wherein the 4-substituent is an ionic or hydrophilic moiety. Such ionic or hydrophilic moieties include but are not limited to those moieties selected from the group consisting of hydroxyl groups, carboxyl groups, and carboxylic acid salt groups. Useful water-soluble benzophenones include but are not limited to those selected from the group consisting of 4-trimethylaminomethyl benzophenone hydrochloride and benzophenone sodium 4-methanesulfonate. Useful water-soluble thioxanthones include but are not limited to those selected from the group consisting of 3-(2-hydroxy-3-trimethylaminopropoxy) thioxanthone hydrochloride, 3-(3-trimethylaminopropoxy) thioxanthone hydrochloride, thioxanthone 3-(2-ethoxysulfonic acid) sodium salt, and thioxanthone 3-(3-propoxysulfonic acid) sodium salt. Useful water-soluble phenyl ketones include but are not limited to those selected from the group consisting of (2-hydroxy-2-propyl) (4-diethylene glycol phenyl) ketone, (2-hydroxy-2-propyl) (phenyl-4-butanecarboxylate) ketone, 4-(2-hydroxethoxy) phenyl-(2-propyl) ketone, and their water-soluble salts. A preferred water-soluble photoinitiator is 4-trimethylaminomethyl benzophenone hydrochloride.

The aqueous phase may comprise about 0.05 to about 1 part by weight of a photoinitiator, when used, and preferably about 0.1 to about 1 part by weight based on 100 parts by weight of total (co)polymerizable species in the microemulsion.

I.c.ii. Water-Soluble Thermal Initiators

Water-soluble thermal initiators useful in the present invention are initiators which, on exposure to heat, generate free-radicals which initiate (co)polymerization of the hydrophilic monomer(s), the oleophilic monomer(s), the (co)polymerizable oligomer and, when present, the (co)polymerizable surfactant, as detailed below. Suitable water-soluble thermal initiators include but are not limited to those selected from the group consisting of potassium persulfate, ammonium persulfate, sodium persulfate, and mixtures thereof; oxidation-reduction initiators such as the reaction product of the above-mentioned persulfates and reducing agents such as those selected from the group consisting of sodium metabisulfite and sodium bisulfite; and 4,4'-azobis (4-cyanopentanoic acid) and its soluble salts (e.g., sodium, potassium). The preferred water-soluble thermal initiator is ammonium persulfate. Preferably, most water-soluble thermal initiators are used at temperatures of from about 50° to about 70° C., while the oxidation-reduction-type initiators are used at temperatures of from about 30° to about 50° C. When used, water-soluble thermal initiators may comprise from about 0.05 to about 1 part by weight, preferably about 0.1 to about 1 part by weight based on 100 parts by weight of (co)polymerizable species in the microemulsion.

I.d. Water-Soluble Additives

The aqueous phase may optionally further comprise various water-soluble additive(s) in order to produce a polymerized microemulsion PSA having specific properties and/or appearance. Each additive is selected to produce a desired end-product. For example, if a conductive polymer is desired, an electrolyte can be added. If a pigmented polymer is desired, a dye can be added. Examples of useful additives include but are not limited to those selected from the group consisting of water-soluble crosslinkers (such as methylene bisacrylamide), plasticizers (such as glycerin and polyalkylene glycols), pH adjusters, electrolytes, dyes, pigments, pharmaceutically-active compounds, physiologically-active compounds, cosolvents, noncopolymerizable polar oligomers, mixtures thereof, and the like. In particular, electrolytes including but not limited to those selected from the group consisting of potassium chloride, lithium chloride, sodium chloride, and mixtures thereof have been found to be useful in various formulations of the present invention when it is desired that the polymerized microemulsion PSA exhibit electrical conductivity. Up to about 10 parts by weight of an electrolyte can be included, preferably about 0.5 parts by weight to about 5 parts by weight based on 100 parts by weight of the total aqueous phase.

Noncopolymerizable polar oligomers useful as additives include but are not limited to those selected from the group consisting of poly(N-vinylpyrrolidone), polyethylene glycols, poly(oxyethylene) alcohols, poly(ethylimine), and mixtures thereof. Such oligomers are added to affect the bulk properties of the resulting polymerized microemulsion PSA, e.g., to impart hydrophilic properties to the material.

Typical cosolvents include but are not limited to those selected from the group consisting of aliphatic alcohols having from about 1 to about 8 carbon atoms (such as glycerin), polyethers (such as Butyl Cellosolve™, Butyl Carbitol™, Hexyl Cellosolve™, and Hexyl Carbitol™ all commercially available from Union Carbide), and mixtures thereof.

It will be readily recognized that essentially all organic water soluble additives which are added to the aqueous phase will exhibit a degree of solubility in the organic phase of the microemulsion. Each additive has its own distribution ratio between the aqueous phase and the organic phase. Thus, unless otherwise specified, the above-mentioned constituents of the aqueous phase will be found in and will affect the properties of the organic phase also. It is not necessary to the understanding and practice of the present invention to quantify the particular distribution ratio of each and every additive mentioned heretofore.

II. Oil Phase

The terms "organic phase", "oil phase", and "lipophilic phase" are used interchangeably herein.

Prior to commencing polymerization, the oil phase of the microemulsion comprises hydrophobic free-radically (co) polymerizable monomers suitable for forming a hydrophobic pressure sensitive adhesive homopolymer or copolymer, free radically (co)polymerizable polar monomer, oil-soluble initiator, and optional reactive lipophilic additives.

II.a. Hydrophobic Free-Radically (Co)Polymerizable Monomers

Hydrophobic free-radically polymerizable, ethylenically-unsaturated monomers useful in the lipophilic phase of the microemulsions of the present invention include but are not limited to those selected from the group consisting of about $C_1$ to about $C_{18}$ alkyl esters of acrylic acid, i.e., those esters derived from acrylic acid and about $C_1$ to about $C_{18}$ alcohols, provided that such monomers are suitable for forming a hydrophobic polymer having pressure sensitive adhesive properties.

The glass transition temperature (Tg) of the resulting polymerized microemulsion PSA can be determined according to techniques known to those skilled in the art. The Tg of the resulting polymerized microemulsion PSA is contributed by selection of hydrophobic monomers suitable for forming a hydrophobic polymer having pressure sensitive adhesive properties. A Tg of less than about 10° C. will frequently provide a resulting hydrophobic polymer having pressure sensitive adhesive properties. A Tg of less than about 0° C. will more frequently provide a resulting hydrophobic polymer having pressure sensitive adhesive properties. A Tg of less than about −10° C. will most frequently provide a resulting hydrophobic polymer having pressure sensitive adhesive properties.

Of these possible hydrophobic monomer candidates, alkyl acrylates include those selected from the group consisting of isooctyl acrylate, 2-ethylhexyl acrylate, and n-butyl acrylate are particularly preferred because of their availability for use and because of the Tg of the resulting hydrophobic polymer formed from such hydrophobic monomers.

The organic phase may further optionally comprise free-radically polymerizable ethylenically-unsaturated comonomers which are copolymerizable with the alkyl acrylate monomers described above in order to modify the glass transition temperature (Tg) of the resulting polymerized microemulsion PSA, from that Tg contributed by the hydrophobic monomer(s). Preferred comonomers include those selected from the group consisting of styrene, acrylonitrile, and vinyl esters (such as vinyl acetate, vinyl propionate and vinyl neopentanoate, etc.) with the selection of the comonomer dependent on the properties desired of the final solid bicontinuous polymer.

The polymerized microemulsion PSA of the present invention comprises from about 5 to about 80 percent by weight of hydrophobic monomers, preferably from about 10 to about 70 percent by weight, and most preferably from about 12 to about 60 percent by weight based on the total weight of the microemulsion, in order to impart sufficient strength, cohesiveness, and pressure sensitive adhesive properties to the resulting polymerized microemulsion PSA prepared therefrom.

As has been stated previously, the percent composition of each constituent of the microemulsion will be determined by the skilled practitioner based on the desired pressure sensitive adhesive properties of the copolymer. The Examples infra and the phase diagrams of FIGS. 1–4 further explain and exemplify how the choice of ratios of constituents is made.

II.b. Free-Radically (Co)Polymerizable Polar Monomer

The organic phase of the microemulsion will contain a portion of the free-radically polymerizable polar monomers described under I.b.ii. and I.b.iii., above, if used, because of the partitioning of such organic materials between the aqueous phase and the organic phase of a microemulsion, as described previously. Each monomer described therein exhibits its own distribution ratio, the enumeration of which is not necessary for the understanding and practicing of the present invention.

II.c. Oil-Soluble Initiators

The oil phase comprises an oil-soluble free-radical photopolymerization initiator ("photoinitiator") and optionally further comprises a thermal initiator.

II.c.i. Oil-Soluble Photoinitiators

Oil-soluble photoinitiators which are useful according to the present invention are those which generate free radicals on exposure to electromagnetic (usually ultraviolet) radiation which act as initiators for the (co)polymerization of the hydrophilic monomer(s) and/or oligomer(s), the oleophilic monomer(s), and, when present, the (co)polymerizable surfactant. Useful photoinitiators include, but are not limited to those selected from the group consisting of: 1) mixtures of Michler's ketone and benzil or benzophenone, preferably in a weight ratio of about 1:4; 2) coumarin-based photoinitiator systems as described in U.S. Pat. No. 4,289,844, incorporated by reference herein; and, preferably, 3) systems based on dimethoxyphenylacetophenone and/or diethoxyacetophenone. The oil-soluble photoinitiators are included in the microemulsions as part of the organic phase, initially. On irradiation, the free-radicals thus generated effect (co) polymerization of monomers in both the aqueous and the organic phases, as well as copolymerization of the (co) polymerizable surfactant.

The organic phase comprises about 0.01 to about 5 parts by weight of an oil soluble photoinitiator, based on 100 parts by weight of total (co)polymerizable species in the microemulsion.

II.c.ii. Optional Oil-Soluble Thermal Initiators

Oil-soluble thermal initiators may optionally be used in the preparation of the bicontinuous polymers of the present invention subsequent to the photopolymerization step as described above in order to complete the polymerization reaction.

Oil-soluble thermal initiators useful in the present invention are initiators which, on exposure to heat, generate free radicals which initiate (co)polymerization of the hydrophilic monomer(s), oligomer(s) the oleophilic monomer(s), and, when present, the polymerizable surfactant, as detailed below. Suitable oil-soluble thermal initiators include but are not limited to those selected from the group consisting of azo compounds such as Vazo 64™ (2,2'-azobis(isobutyronitrile) and Vazo 52™ (2,2'-azobis(2,4-dimethylpentanenitrile)), both available from dupont, peroxides such as benzoyl peroxide and lauroyl peroxide, and mixtures thereof. The preferred oil-soluble thermal initiator is (2,2'-azobis (isobutyronitrile)).

The organic phase may comprise about 0 to about 5 parts by weight of an oil-soluble thermal initiator, typically about 0.05 to about 5 parts by weight when used, preferably about 0.1 to about 5 parts if used, based on 100 parts of total weight of (co)polymerizable compounds in the microemulsion.

II.d. Optional Reactive Lipophilic Additives

The organic phase may optionally further comprise one or more additional free-radically reactive constituents, including, but not limited to those selected from the group consisting of oil-soluble crosslinking agents, chain transfer agents, and mixtures thereof. Examples of useful crosslinking agents include but are not limited to those selected from the group consisting of divinylbenzene; about $C_4$ to about $C_8$ alkyl diacrylates such as those selected from the group consisting of 1,4-butanediol diacrylate, 1,6-hexanediol diacrylate, 1,8-octanediol diacrylate; and mixtures thereof. The preferred crosslinking agent is 1,6-hexanediol diacrylate. The crosslinking agent, if added, changes the physical properties, such as cohesive strength, of the final polymer. The organic phase optionally further comprise about 0 to about 10 or more, parts by weight crosslinker, typically, if used, about 0.1 to about 2 percent by weight, based on 100 parts by weight of the total oil phase. The amount of crosslinker used will determine the physical properties of the polymer, such as insolubility in solvents, modulus, and internal strength. For such applications, the organic phase typically comprises about 0.1 to about 5 parts by weight of a crosslinker, based on 100 parts by weight of the oil phase. One of ordinary skill in the art will be able to determine the proper amount of crosslinker to obtain desired physical properties, and such an artisan will understand that there is no practical upper limit on the amount of crosslinker which can be used in the formulations of the present invention.

The organic phase may optionally further comprise a chain transfer agent. Examples of useful chain transfer agents include but are not limited to those selected from the group consisting of carbon tetrabromide, alcohols, mercaptans, and mixtures thereof. When present, the preferred chain transfer agent is isooctylthioglycolate. The oil phase may further comprise up to about 0.5 parts by weight of a chain transfer agent, typically about 0.01 weight percent to about 0.5 parts by weight, if used, preferably about 0.05 parts by weight to about 0.2 parts by weight, based upon 100 parts by weight of the total oil phase.

II.e. Optional Nonreactive Lipophilic Additives

The oil phase may optionally further comprise one or more nonreactive oil-soluble additives. A variety of nonreactive oil-soluble additives may be included in the microemulsion. These materials are added to produce a final polymer system with specified physical properties or appearance. Examples of such optional oleophilic additives include but are not limited to those selected from the group consisting of plasticizers, such as one of the phthalate esters well-known in the art. The oil phase may optionally further comprise about 0 to about 20 parts by weight of a plasticizer, typically about 5 to about 20 parts by weight if used, preferably about 8 to about 15 weight percent based on 100 parts by weight of the oil phase.

Surfactants

Nonionic and ionic (anionic and cationic) surfactants employed in the present invention to prepare microemulsions are discussed below. The surfactant(s) can be copolymerizable with the monomers present in the microemulsion or non-copolymerizable. The surfactant(s) are preferably copolymerizable so that the resulting polymerized microemulsion PSA is less sensitive to water. When resistance to water is not required, non-copolymerizable surfactants are preferred due to their generally lower cost.

I. Nonionic Surfactants

The nonionic surfactants are usually condensation products of an organic aliphatic or alkylaromatic hydrophobic compound and an alkylene oxide, such as ethylene oxide, which is hydrophilic. Almost any hydrophobic compound having a carboxy, hydroxy, amido, or amino group with a free hydrogen present can be condensed with ethylene oxide to form a nonionic surfactant. The length of the ethylene oxide chain of the condensation product can be adjusted to achieve the desired balance between the hydrophobic and hydrophilic elements (Hydrophilic-Lipophilic Balance or HLB). The HLB of a surfactant is an expression of the balance of the size and strength of the hydrophilic (water-loving or polar) and the lipophilic (oil-loving or non-polar) groups of the surfactant. The useful HLB of nonionic surfactants for the present invention to prepare microemulsions is from about 6 to about 19, preferably from about 9 to about 18, and most preferably from about 10 to about 16. Useful nonionic surfactants include those selected from the group consisting of non(co)polymerizable nonionic surfactants, ethylenically-unsaturated copolymerizable nonionic surfactants, and mixtures thereof.

1.a. Non(co)polymerizable Nonionic Surfactants

Particularly suitable nonreactive nonionic surfactants include but are not limited to those selected from the group consisting of the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles, most preferably about 5 to about 20 moles of ethylene oxide to achieve the above defined HLB. Examples of such nonionic ethoxylated fatty alcohol surfactants are the Tergitol™ 15-S series from Union Carbide and Brij™ surfactants from ICI. Tergitol™ 15-S Surfactants include $C_{11-C15}$ secondary alcohol polyethyleneglycol ethers. Brij™ 58 Surfactant is Polyoxyethylene(20) cetyl ether, and Brij™ 76 Surfactant is Polyoxyethylene(10) stearyl ether.

Other suitable nonreactive nonionic surfactants include but are not limited to those selected from the group consisting of the polyethylene oxide condensates of one mole of alkyl phenol containing from about 6 to 12 carbon atoms in a straight or branched chain configuration, with about 3 to about 100 moles, preferably about 5 to about 40 moles, most preferably about 5 to about 20 moles of ethylene oxide to achieve the above defined HLB. Examples of nonreactive nonionic surfactants are the Igepal™ CO and CA series from Rhone-Poulenc. Igepal™ CO surfactants include nonylphenoxy poly(ethyleneoxy) ethanols. Igepal™ CA surfactants include octylphenoxy poly(ethyleneoxy) ethanols.

Another group of usable nonreactive nonionic surfactants include but are not limited to those selected from the group consisting of block copolymers of ethylene oxide and propylene oxide or butylene oxide with HLB values of about 6 to about 19, preferably about 9 to about 18, and most preferably about 10 to about 16. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers.

Still other satisfactory nonreactive nonionic surfactants include but are not limited to those selected from the group consisting of sorbitan fatty acid esters, polyoxyethylene sorbitan fatty acid esters and polyoxyethylene stearates having HLBs of about 6 to about 19, preferably about 9 to about 18, and most preferably about 10 to about 16. Examples of such fatty acid ester nonionic surfactants are the Span™, Tween™, and Myrj™ surfactants from ICI. Span™ surfactants include $C_{12}$–$C_{18}$ sorbitan monoesters. Tween™ surfactants include poly(ethylene oxide) $C_{12}$–$C_{18}$ sorbitan monoesters. Myrj™ surfactants include poly(ethylene oxide) stearates.

1.b. Ethylenically-Unsaturated Copolymerizable Nonionic Surfactants

Suitable nonionic surfactants for incorporation in the microemulsions of this invention are ethylenically-unsaturated copolymerizable nonionic surfactants including but not limited to those selected from the group consisting of those falling within the general formula:

$$R\text{—}O\text{—}(R'O)_m\text{—}(EO)_{(n-1)}\text{—}CH_2CH_2OH$$

where R is selected from the group consisting of (about $C_2$ to about $C_{18}$) alkenyl, acrylyl, acrylyl (about $C_1$ to about $C_{10}$) alkyl, methacrylyl, methacrylyl (about $C_1$ to about $C_{10}$) alkyl, vinylphenyl and vinylphenylene (about $C_1$ to about $C_6$) alkyl; R'O is selected from the group consisting of bivalent alkyleneoxy groups derived from epoxy compounds having more than two carbon atoms, preferably three or four carbon atoms, such as those selected from the group consisting of propylene oxide, butylene oxide, etc. and combinations thereof; E is a bivalent ethylene radical; m represents an integer of about 5 to about 100; n represents an integer of about 5 to about 100; the ratio of m and n being from about 20:1 to about 1:20. Varying the ratio of m and n will vary the HLB of the polymerizable surfactant. The required HLB for the nonionic surfactant(s) of the present invention is from about 6 to about 19, preferably from about 9 to about 18, and most preferably from about 10 to about 16. Examples of such copolymerizable nonionic surfactants are the alkylene polyalkoxy ethanol surfactants available from PPG Industries under the tradenames Mazon BSN™ 185, 186 and 187. Mazon BSN™ surfactants include alkylene polyalkoxy ethanol.

2. Anionic Surfactants

Anionic surfactants normally include a hydrophobic moiety selected from the group consisting of (about $C_6$ to about $C_{20}$) alkyl, alkylaryl, and alkenyl groups and an anionic group selected from the group consisting of sulfate, sulfonate, phosphate, polyoxyethylene sulfate, polyoxythylene sulfonate, polyoxethylene phosphate and the alkali metal salts, ammonium salts, and tertiary amino salts of such anionic groups. A particular ethylenically-unsaturated copolymerizable surfactant which includes (about $C_2$ to about $C_{18}$) alkenyl polyoxypropylene or (about $C_2$ to about $C_{18}$) polyoxybutylene as a hydrophobic moiety and an anionic group of polyoxyethylene sulfate is also useful in the present invention to prepare microemulsions. Examples of additional anionic surfactants which are useful in the present invention are discussed below.

2.a. Nonreactive Anionic Surfactants

Nonreactive anionic surfactants which can he used in the present invention include but are not limited to those selected from the group consisting of (about $C_6$ to about $C_{20}$) alkyl or alkylaryl sulfates or sulfonates such as sodium lauryl sulfate (commercially available as Polystep™ B-3 from Stepan Co.) and sodium dodecyl benzene sulfonate, (commercially available as Siponate™ DS-10 from Rhone-Poulenc); polyoxyethylene (about $C_6$ to about $C_{20}$) alkyl or alkylphenol ether sulfates with the ethylene oxide repeating unit in the surfactant below about 30 units, preferably below about 20 units, most preferably below about 15 units, such as Polystep™ B-1 commercially available from Stepan Co. and Alipal™ EP110 and 115 from Rhone-Poulenc; (about $C_6$ to about $C_{20}$) alkyl or alkylphenoxy poly(ethyleneoxy)ethyl mono-esters and di-esters of phosphoric acid and its salts, with the ethylene oxide repeatling unit in the surfactant below about 30 units, preferably below about 20 units, most preferably below about 15 units, such as Gafac™ PE-510 and Gafac™ RE-610 from GAF.

2.b. Ethylenically-Unsaturated Copolymerizable Anionic Surfactants

Suitable anionic surfactants for incorporation in the microemulsions of this invention include but are not limited to those selected from the group consisting of ethylenically-unsaturated copolymerizable surfactants of the formula:

$$R\text{—}O\text{—}(R'O)_m\text{—}(EO)_{n-1}\text{—}CH_2CH_2X$$

where R is selected from the group consisting of about $C_2$ to about, $C_{18}$ alkenyl, acrylyl, acrylyl (about $C_1$ to about $C_{10}$) alkyl, methacrylyl, methacrylyl (about $C_1$ to about $C_{10}$) alkyl, vinylphenyl and vinylphenylene (about $C_1$ to about $C_6$) alkyl; R'O is selected from the group consisting of bivalent alkyleneoxy groups derived from epoxy compounds having more than two carbon atoms, preferably three or four carbon atoms, such as propylene oxide and butylene oxide and mixtures of such alkyleneoxy groups; E is a bivalent ethylene radical; m represents an integer of about 5 to about 100, R represents an integer of about 5 to about 100; the ratio of m and n being from about 20:1 to about 1:20. Varying the ratio of m and n will vary the HLB of the polymerizable surfactant. The required HLB for the anionic copolymerizable surfactants of the present invention, exclusive of the X-group, is from about 3 to about 16. X is an anionic group selected from the group consisting of sulfonate, sulfate, phosphate, and alkali metal salts or ammonium salts or tertiary amino salts of such anionic groups. An example of such a copolymerizable anionic surfactant is Mazon™ SAM 211 from PPG Industries, Inc.

3. Cationic Surfactants

Cationic surfactants useful in the present invention include but are not limited to those selected from the group consisting of quaternary ammonium salts in which at least one higher molecular weight group and two or three lower molecular weight groups are linked to a common nitrogen atom to produce a cation, and wherein the electrically-balancing anion is selected from the group consisting of a halide (bromide, chloride, etc.), acetate, nitrite, and lower alkosulfate (methosulfate etc.). The higher molecular weight substituent(s) on the nitrogen is/are often (a) higher alkyl group(s), containing about 10 to about 20 carbon atoms, and the lower molecular weight substituents may be lower alkyl of about 1 to about 4 carbon atoms, such as methyl or ethyl, which may be substituted, as with hydroxy, in some instances. One or more of the substituents may include an aryl moiety or may be replaced by an aryl, such as benzyl or phenyl. Among the possible lower molecular weight substituents are also lower alkyls of about 1 to about 4 carbon atoms, such as methyl and ethyl, substituted by lower polyalkoxy moieties such as polyoxyethylene moieties, bearing a hydroxyl end group, and falling within the general formula—$R(CH_2CH_2O)_{(n-1)}CH_2CH_2OH$ where —R is $C_{1-4}$ divalent alkyl group bonded to the nitrogen, and n represents an integer of about 1 to about 15. Alternatively, one or two of such lower polyalkoxy moieties having terminal hydroxyls may be directly bonded to the quaternary nitrogen instead of being bonded to it through the previously mentioned lower alkyl. Examples of useful quaternary ammonium halide surfactants for use in the present invention include but are not limited to those selected from the group consisting of methylbis(2-hydroxyethyl)coco-ammonium chloride or oleyl-ammonium chloride, (Ethoquad™ C/12 and O/12, respectively) and methyl polyoxyethylene (15) octadecyl ammonium chloride (Ethoquad™ 18/25) from Akzo Chemical Inc.

In the microemulsions of the present invention, the concentrations of the components are typically as follows, expressed in weight-percent:

TABLE A*

| MICROEMULSION | USEFUL | PREFERRED | MOST PREFERRED |
|---|---|---|---|
| Hydrophobic Monomer | 5–80% | 10–70% | 12–60% |
| Water | 2–60% | 5–40% | 5–30% |
| Hydrophilic or Amphiphilic Monomer or Oligomer | 5–80% | 5–70% | 10–60% |
| Surfactant | 2–40% | 2–30% | 2–20% |

*The numerical values should be read such that the term "about" is inserted before each numerical value. All percentages are by weight and are based on the total weight of the microemulsion. The concentration of each component is chosen such that the total is 100%.

Process for Making Microemulsion

The method of making the microemulsions of the present invention is relatively straight forward because they tend to form spontaneously with little need for vigorous mixing.

As explained above, mixing of the components can be conducted in a convenient order to determine the appropriate weight percents to form the microemulsion.

The following chart shows the preferred order of mixing:

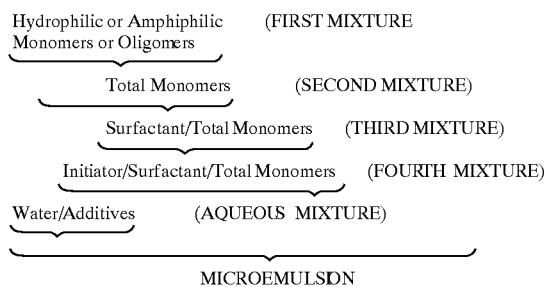

When the preferred amphiphilic monomers/oligomers of acrylic acid and polyethylene glycol acrylate, respectively, are used, an acceptable weight ratio of acrylic acid/polyethylene glycol acrylate ranges from about 0/100 to about 100/0, and preferably about 30/70, to form the first mixture of amphiphilic monomers.

When the preferred hydrophobic monomer of isooctyl acrylate is used with the preferred amphiphilic monomers/oligomers of the first mixture, an acceptable weight ratio of hydrophobic monomer to amphiphilic monomers ranges from about 80/20 to about 10/90, and preferably about 30/70, to form the second mixture of total monomers.

When the preferred surfactant of Brij™ 76 is used with the preferred total monomers of the second mixture, an acceptable weight ratio of surfactant to total monomers ranges from about 5/95 to about 30/70 and preferably about 15/85, to form a third mixture of surfactant/total monomers.

When the preferred initiator of 2,2-dimethoxy-2-phenylacetophenone (also known as 2,2-dimethoxy-2-phenyl-1-phenylethananone or benzildimethylketal) is used with the preferred surfactant/total monomers of the third mixture, an acceptable weight ratio of initiator to surfactant/total monomers ranges from about 0.01/99.99 to about 2/98 and preferably about 0.3/99.7, to form a fourth mixture of initiator/surfactant/total monomers.

When a preferred electrolyte additive is used in water, preferably deionized, an acceptable weight ratio of electrolyte to water ranges from about 0.01/99.99 to about 10/90 and preferably about 4/96, to form an aqueous mixture.

When the preferred components are mixed together to form a microemulsion, an acceptable weight ratio of aqueous mixture to fourth mixture of initiator/surfactant/total monomers ranges from about 5/95 to about 40/60 and preferably about 18/82, to form a microemulsion useful in the present invention.

Using the preferred weight percents in the various mixtures to the total microemulsion, a preferred microemulsion contains about 12.4 weight percent acrylic acid; about 29.2 weight percent polyethylene glycol acrylate; about 27.8 weight percent isooctyl acrylate; about 12.3 weight percent Brij™ 76 surfactant; about 0.3 weight percent initiator; about 0.7 weight percent electrolyte; and about 17.3 weight percent water.

This mixture of ingredients forms a microemulsion well within the microemulsion region of a three phase diagram that was based on an initial 15 weight percent of surfactant prior to mixing of later components. Because of the selection of isooctyl acrylate as the hydrophobic monomer, bulk pressure sensitive adhesive properties are provided by the hydrophobic monomer to the polymerized microemulsion PSA of the invention.

According to the techniques described herein, one skilled in the art will be able to easily determine the appropriate microemulsion region from which a polymerized microemulsion PSA can be polymerized.

As a result of the order of mixing and the weight percents of each mixture preliminary to forming the microemulsion, the final weight percents of the components in the microemulsion can vary significantly within acceptable ranges. To assist one skilled in the art in the formation of microemulsions, diagrams can be employed using the four essential components of water, hydrophobic monomer(s), hydrophilic or amphiphilic monomer(s) or oligomer(s), and surfactant and given weights of some of the components prior to mixing of the remaining components.

For example, a four component diagram is seen in FIG. 1 with apex A representing 100% of hydrophobic monomers, apex B representing 100% of surfactant, apex D representing 100% of hydrophilic or amphiphilic monomers or oligomers, and apex C representing 100% water. This four component diagram could be unwieldy to use to prepare microemulsion diagrams. However, if one component, surfactant, is maintained at a constant weight (e.g., about 15 weight percent prior to addition of water), an equilaterally triangular slice of the four component diagram results.

However, an equilaterally triangular slice of a four component diagram does not respect changes in weight percent as additional components are added if sequential mixing is employed to determine the microemulsion region of a final mixture.

Figure 2:
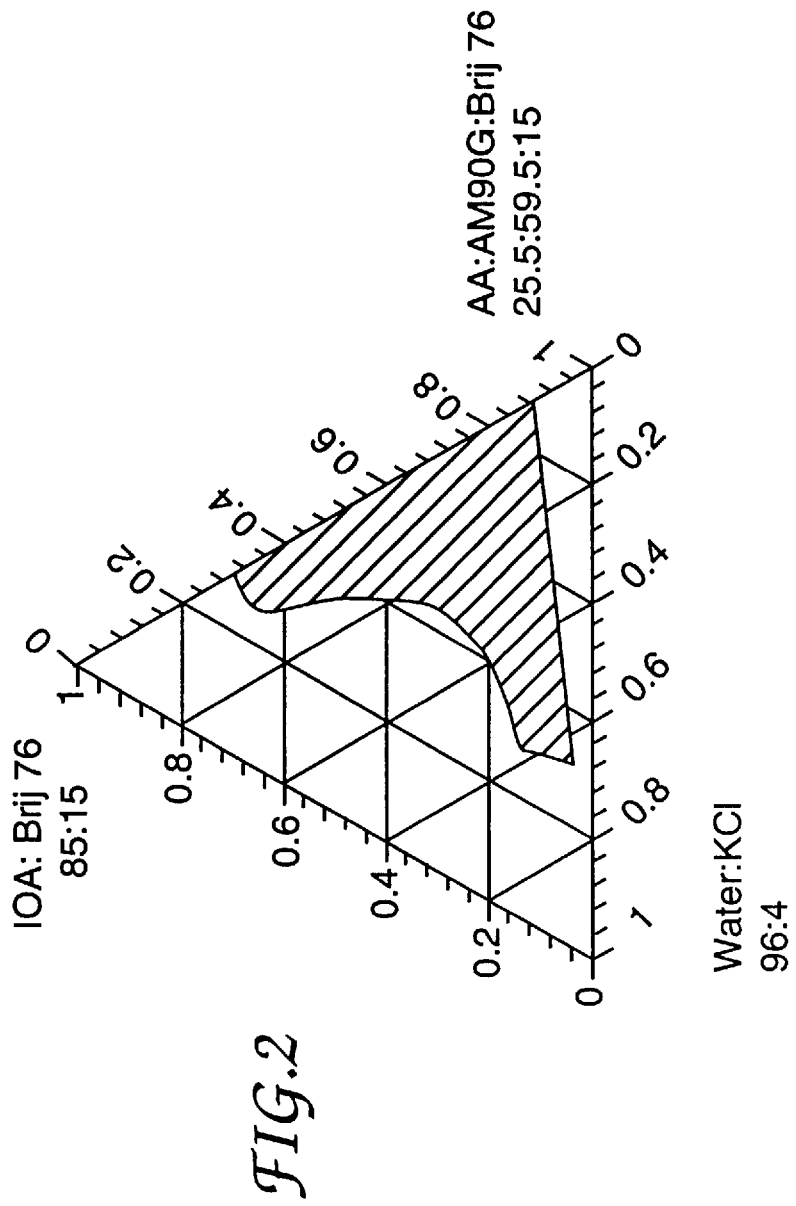
FIG. 2 is a three component diagram, showing a clear microemulsion area within which reside preferred compositions of the present invention prepared according to Examples 1–7 described below.
Figure 3:
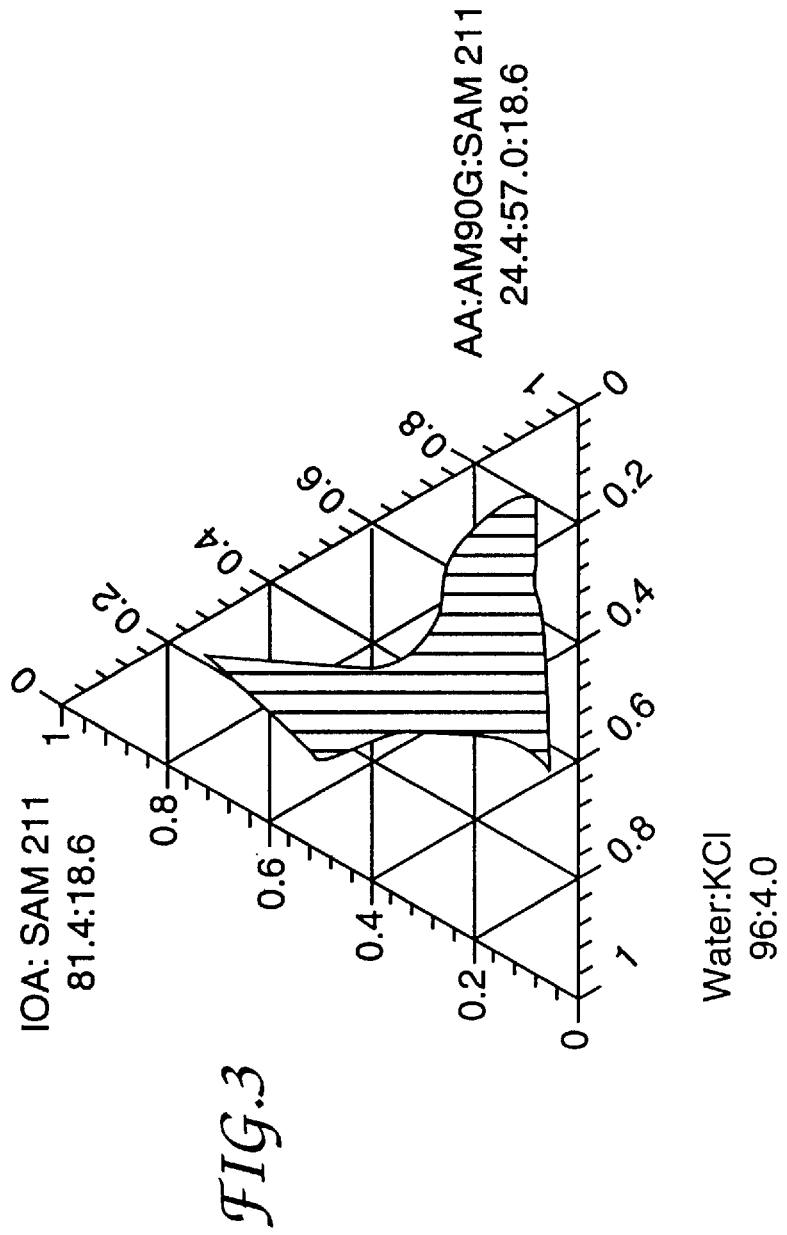
FIG. 3 is a three component diagram, showing a clear microemulsion area within which reside other compositions of the present invention prepared according to Example 21 described below.
Figure 4:
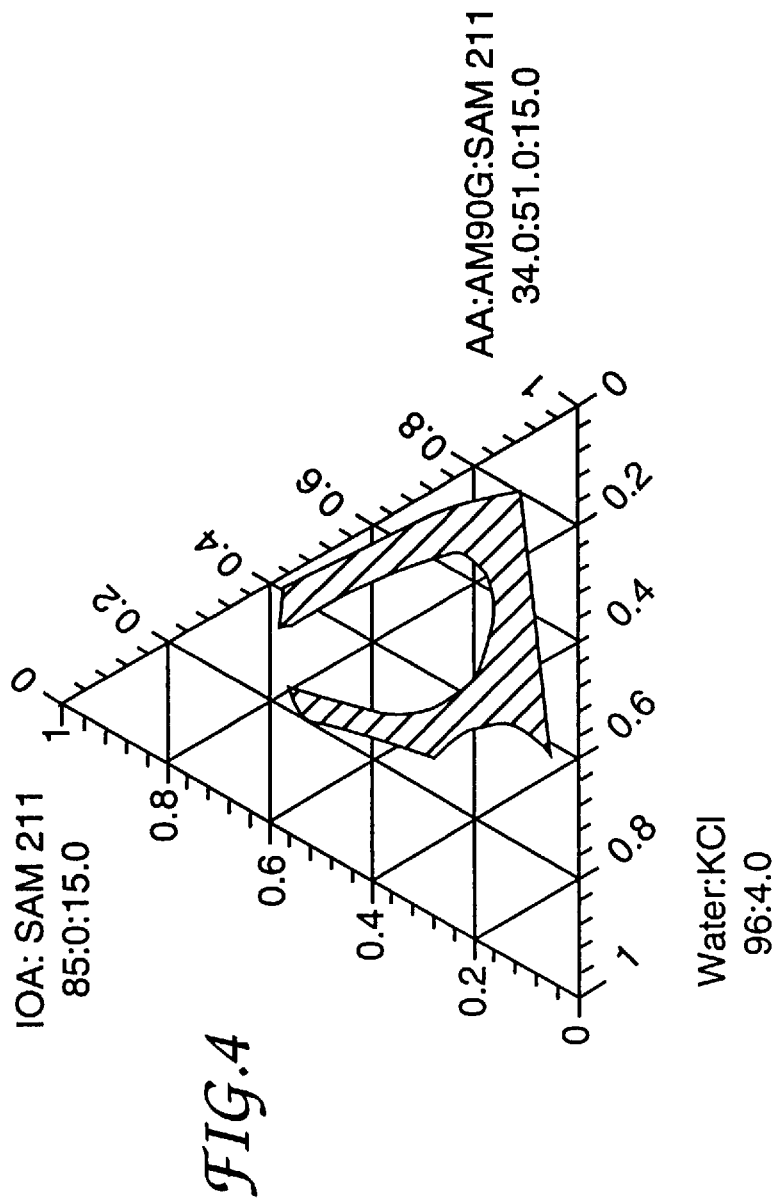
FIG. 4 is a three component diagram, showing a clear microemulsion area within which reside other compositions of the present invention prepared according to Example 28 described below.

Therefore, one method of the present invention employs a different triangular slice, as shown striped in FIG. 1. A microemulsion region of a mixture can be determined via titration of one essential component, water (including any water-borne additives), into a given amount of surfactant (along line X-Y) and a full range of given weight ratios of monomer(s)/oligomer(s), the three phase diagrams shown in FIGS. 2–4 are represented in FIG. 1 as starting at a given surfactant weight percent and a given ranges of weight ratios of hydrophobic monomer(s)/hydrophilic or amphiphilic monomer(s) or oligomer(s) that represents (1) a line X-Y on one face A-B-D of the four component diagram representing 0 weight percent water at a given surfactant weight percent and (2) extends in a plane toward the point comprising 100 weight percent water. Thus, the triangular slice used in the present invention is the triangular plane having apexes X, Y, and C.

The triangular slice X-Y-C is not equilateral but provides additional information about the relationship of water (including any water-borne additives) titrated to form a microemulsion in an existing mixture of a given weight of surfactant and monomer(s) or oligomer(s).

Once the amount of each component is known, then the mixing to form the microemulsion on batch basis can occur in the same order. Alternatively, it is desirable to pre-dissolve the oil-soluble photoinitiator in the hydrophobic monomer(s) and to pre-dissolve any water-soluble additives or an oil insoluble ionic monomer or a water soluble photoinitiator in water to form a solution. Then, the hydrophobic monomer mixture and the water solution are admixed with polar monomer, surfactant, and any other optional additives, to make clear and homogeneous microemulsions without phase separation on aging. It is not necessary to employ heat and most mixings are preferably carried out at about room temperature (20°–30° C.). However, higher temperatures could be used depending on whether the microemulsion is stable at the elevated temperature.

The phase transformation between a one-phase clear microemulsion and a two phase turbid emulsion of the present invention is illustrated in FIGS. 2–4 which show, by way of example only, three-phase diagrams for the concentration of hydrophobic or amphiphilic monomers or oligomers, hydrophobic monomers, and water at a given surfactant (polymerizable or non-polymerizable) for certain microemulsions.

While not limited to any particular theory, it is believed that amphiphilic monomers are preferred in the formation of both the hydrophobic polymer PSA continuous phase and the hydrophilic polymer continuous phase. For example, it is known that isooctyl acrylate/acrylic acid copolymers form excellent pressure sensitive adhesives, as disclosed in U.S. Pat. No. Re 24,906 (Ulrich). It is also known that acrylic acid homopolymers, when plasticized and including electrolytes, form excellent ionically conductive pressure sensitive adhesives, as disclosed in U.S. Pat. No. 4,539,996 (Engel). Use of acrylic acid or another amphiphilic monomer that can copolymerize to form a hydrophobic pressure sensitive adhesive or can homopolymerize to form a hydrophilic pressure sensitive adhesive when plasticized, is particularly preferred. Further, use of an amphiphilic oligomer, such as polyethylene glycol acrylate, is particularly preferred to provide a substantially nonporous biphasic composition that is pressure sensitive adhesive in at least its hydrophobic continuous phase.

FIG. 2 is a phase diagram, showing both a clear microemulsion area and a turbid emulsion area for preferred compositions of the present invention described in Examples 1–7 below, in which the surfactant is a polymerizable nonionic surfactant, Brij™ 76, available from Sigma Chemicals present at a fixed weight percent of 15 prior to the addition of any aqueous component (i.e., various points along line X-Y in FIG. 1) and the hydrophilic or amphiphilic monomers or oligomers phase is a mixture of acrylic acid and a polyoxyethylene acrylate (AM90G Ester, available from Shin-Nakamura Chemical Co.) in a weight ratio of 30:70 acrylic acid:acrylate, the hydrophobic polymerizable monomer is isooctyl acrylate, and the aqueous mixture is a 4 weight percent aqueous solution of potassium chloride in deionized water. The shaded area of FIG. 2 indicates the range of concentrations over which microemulsions according to the present invention to be used in the formation of polymerized microemulsion PSA's.

FIG. 3 is a phase diagram, showing both a clear microemulsion area and a turbid emulsion area for preferred compositions of the present invention described in Example 21 below, in which the surfactant is a polymerizable anionic surfactant, SAM-211 commercially available from PPG Industries, Inc. present at a fixed weight percent of 18.6 prior to the addition of any aqueous component and the hydrophilic or amphiphilic monomers phase is a mixture of acrylic acid and a polyoxyethylene acrylate (AM90G Ester, available from Shin-Nakamura Chemical Co.) in a weight ratio of 30:70 acrylic acid:acrylate, the hydrophobic polymerizable monomer is isooctyl acrylate, and the aqueous mixture is a 4 weight percent aqueous solution of potassium chloride in deionized water. The shaded area of FIG. 3 indicates the range of concentrations over which microemulsions according to the present invention to be used in the formation of polymerized microemulsion PSA's. FIG. 3 demonstrates that variations of surfactant and concentration of surfactant can affect the resulting clear microemulsion region.

FIG. 4 is a phase diagram, showing both a clear microemulsion area and a turbid emulsion area for preferred compositions of the present invention described in Example 28 below, in which the surfactant is a polymerizable anionic surfactant, SAM-211 commercially available from PPG Industries, Inc. present at a fixed weight percent of 15 prior to addition of any aqueous component and the hydrophilic or amphiphilic monomers phase is a mixture of acrylic acid and a polyoxyethylene acrylate (AM90G Ester, available from Shin-Nakamura Chemical Co.) in a weight ratio of 40:60 acrylic acid:acrylate, the hydrophobic polymerizable monomer is isooctyl acrylate, and the aqueous mixture is a 4 weight percent aqueous solution of potassium chloride in deionized water. The shaded area of FIG. 4 indicates the range of concentrations over which microemulsions according to the present invention to be used in the formation of polymerized microemulsion PSA's. FIG. 4 demonstrates that variations of ratio of acrylic acid and acrylate, compared with the microemulsion shown in FIG. 2, can affect the resulting clear microemulsion region.

Once the microemulsion is obtained, polymerization occurs via free radical polymerization initiated by irradiation according to techniques known to those skilled in the art.

The microemulsion is then coated onto a flexible carrier web using any conventional means such as roller coating, dip coating, knife coating, or extrusion coating and subsequently polymerized in an inert atmosphere, i.e., oxygen free, such as using a nitrogen atmosphere as is well known in the art.

The microemulsion can also be polymerized in air by the microemulsion with a plastic film, preferably polyester having a silicone release surface contacting the microemulsion, which is substantially transparent to ultraviolet radiation, but impervious to oxygen, and subsequently irradiating the microemulsion through that film using fluorescent-type ultraviolet lamps which emit UV light in the wavelength range absorbed by the particular photoinitiator used.

Several different lamps which are commercially available may be used. These include medium pressure mercury lamps and low intensity fluorescent lamps, each having various emission spectra and emission maxima between 280 and 400 nm. For convenience, commercially available fluorescent black lights with a maxima at about 351 nm and 90% of the emissions between 300 and 400 nm are preferably utilized.

In general, the total radiation dose should be between about 200–700 milliJoules/cm$^2$. Maximum efficiency and rate of polymerization is dictated by the relationship between emission properties of the radiation source and the absorption properties of the photoactive compounds employed. It is preferable that at least about 75% of the radiation be between 300 and 400 nm in the event that the preferred photoinitiator, 2,2-dimethoxy-2-phenyl-acetophenone, (also known as 2,2-dimethoxy-2-phenyl-1-phenylethanone and benzildimethylketal), is employed.

The photopolymerization can also be carried out in an inert atmosphere; however, tolerance to oxygen can be increased by including an oxidizable tin compound in the composition as disclosed in U.S. Pat. No. 4,303,485.

One photopolymerization process involves initial exposure of the microemulsion to electromagnetic radiation of from about 280 to 500 nm wavelength and from 0.01 to 20 milliWatts/cm$^2$ average light intensity followed by exposure to electromagnetic radiation of from about 280 to 500 nm wavelength and having an average light intensity of greater than 20 milliWatts/cm$^2$.

Preferably, the photopolymerization process involves continuous exposure of the microemulsion to electromagnetic radiation of about 351 nm for enough time to provide about 680 milliJoules/cm of the microemulsion. About 10 minutes of photopolymerization time is needed in this circumstance. This amount of ultraviolet energy irradiating the microemulsion can be administered continuously or in batches, according to production requirements.

The polymerization of the microemulsion can occur in ambient conditions. Ambient temperature, pressure, and humidity are acceptable.

Once polymerization is complete, water can optionally be removed via evaporation using a convection oven or infrared light sources. In some instances, water must be removed to provide pressure sensitive adhesiveness. In the case where ionic conductivity is desired, it is preferred to provide an in situ, solventless polymerization without removal of water, because presence of water assists in ionic conductivity of the hydrophilic polymer continuous phase.

Usefulness of the Invention

Polymerized microemulsion PSA's of the present invention can be used in a variety of applications where pressure sensitive adhesives are industrially or commercially applied in the manufacture of tapes, adhesive substrates, and the like. Preferably, polymerized microemulsion PSA's of the present invention can be used in the field of health care where adhesive requirements are particularly stringent and difficult when adhesion to mammalian skin is involved.

As stated in the Summary of the Invention, polymerized microemulsion PSA's have defined pressure sensitive adhesive properties using the PSTC-1 Test of at least 3 Newtons/100 mm. These defined pressure sensitive adhesive properties apply whether the polymer is hydrated (i.e., "wet" adhesion) or dehydrated (i.e., "dry" adhesion). Desirably, for high performance adhesion to a variety of surfaces, the pressure sensitive adhesive properties is at least 4 Newtons/100 mm because that amount of 180° peel adhesion strength is needed to provide adequate adhesiveness for almost all commercial adhesive usage.

Preferably for high performance adhesion, the pressure sensitive adhesive properties are at least 10 Newtons/100 mm because tack to a variety of industrial substrates is quite acceptable for general purpose adhesiveness. For high performance adhesion to mammalian skin, the pressure sensitive adhesive properties can be about 15–25 Newtons/100 mm because about 20 Newtons/100 mm provides a tack that is quite acceptable for pressure sensitive adhesive products applied to mammalian skin. For high performance aggressive adhesion, the pressure sensitive adhesive properties can be at least 30, 40, 50, or 60 Newtons/100 mm depending on the 180° peel adhesion strength desired for structural adhesives to a variety of substrates.

With the variety of polymerized microemulsion PSA's possible according to present invention, almost any value of pressure sensitive adhesive properties can be constructed, tailored to meet the needs of the desired usage. The common denominator for these polymerized microemulsion PSA's is their minimum 180° peel adhesion of at least 3 Newtons/100 mm and preferably greater peel adhesion strength. As shown below, the Examples of the present invention, with two exceptions, provide the minimum peel adhesion strength and can approach 200 Newtons/100mm.

The adhesiveness of the present invention is found to exist whether the polymerized microemulsion PSA is hydrated ("wet" adhesion) or partially dehydrated ("dry" adhesion). As shown below, the Examples of the present invention show acceptable adhesion, with two exceptions, to provide the minimum peel adhesion strength for both wet adhesion and dry adhesion.

By comparison using the same PSTC-1 Test and the same number of testing samples, the pressure sensitive adhesive properties of the microemulsion polymer blend disclosed in Example 10 of U.S. Pat. No. 5,238,992 (Outubuddin) does not reach more than 2.5 Newtons/100 mm for either wet adhesion or dry adhesion.

Because mammalian skin is a particularly difficult surface to identify and control acceptable adhesive properties, the polymerized microemulsion PSA of the present invention is particularly suitable for use in mammalian skin covering applications such as biocompatible medical adhesives such as for receipt or delivery of electrical signals at or through mammalian skin, delivery of pharmaceuticals or active agents to or through mammalian skin, or treatment of mammalian skin or mammalian skin openings against the possibilities of infection.

Biomedical Electrodes

Biomedical electrodes employing polymerized microemulsion PSA's of the present invention having electrolyte contained therein are useful for diagnostic, (including monitoring), and therapeutic purposes. In its most basic form, a biomedical electrode comprises a conductive medium contacting mammalian skin and a means for electrical communication interacting between the conductive medium and electrical diagnostic, therapeutic, or electrosurgical equipment.

FIGS. 5 and 6 show either a disposable diagnostic electrocardiogram (ECG or EKG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12. Electrode 10 includes means for electrical communication 16 comprising a conductor member having a conductive interface portion 18 contacting field 14 of conductive medium and a tab portion 20 extending beyond field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical conductor member 16 will comprise a strip of material having a thickness of about 0.05–0.2 millimeters, such as polyester film and have a coating 26 on side 22 of silver/silver chloride of about 2.5–12 micrometers, and preferably about 5 micrometers thick thereon. Presently preferred for conductor member 16 are polyester films commercially available as "Scotchpar" commercially available from Minnesota Mining and Manufacturing Company of St. Paul, Minn. or "Melinex" 505-300, 329, or 339 film from ICI Americas of Hopewell, Va. commercially available as "Mellinex" 505-300, 329, or 339 film from ICI Americas of Hopewell, Va. coated with a silver/silver chloride ink commercially available as "R-300" ink from Ercon, Inc. of Waltham, Mass. A TENS conductor member 16 can be made of a nonwoven web, such as a web of polyester/cellulose fibers commercially available as "Manniweb" web from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on the side opposite side 22 having the conductive coating 26. A surgical tape commercially available from 3M Company as "Blenderm" tape can be employed for this purpose.

Alternatively, conductor member can be a multi-layered construction of a nonconductive, flexible polymeric film having a sulfur-reactive surface, a metallic layer deposited on and interacting with the surface and an optional metallic halide layer, according to the disclosure of copending, coassigned, U.S. patent application Ser. No. 08/062,390 filed May 14, 1993, the disclosure of which is incorporated by reference herein. The conductive interface portion 18 of member 16 comprises a metallic layer deposited on an sulfur-reactive surface on at least the side of polymeric film substrate facing field 14 of the polymerized microemulsion PSA and the optional metallic halide layer coated on the metallic layer and contacting field 14. Because depolarizing is not needed for the mechanical and electrical contact with electrical equipment, optional metallic halide layer does not need to extend to tab portion 20.

Alternatively, conductor member 16 can be a multi-layered construction of a nonconductive, flexible polymeric film, an electrically conductive layer, and a thin, conformable depolarizing layer of inorganic oxide, preferably manganese dioxide. Alternatively, conductor member 16 is a multilayered construction of film with electrically conductive and depolarizing layers blended together. Both of these alternative embodiments can be constructed according to the disclosure of copending, coassigned U.S. patent application Ser. No. 08/189,082, the disclosure of which is incorporated by reference herein. The conductive interface portion of member comprises an electrically conductive layer coated on at least the side of polymeric film facing field 14 of polymerized microemulsion PSA and the thin, depolarizing layer coated on the electrically conductive layer and contacting field 14. Because depolarizing is not needed for the mechanical and electrical contact with electrical equipment, depolarizing layer not extend to tab portion 20.

Non-limiting examples of biomedical electrodes which can use polymerized microemulsion PSA's of the present invention, either as conductive or non-conductive adhesive fields include electrodes disclosed in U.S. Pat. Nos. 4,524, 087; 4,539,996; 4,554,924; 4,848,353 (all Engel); 4,846,185 (Carim); 4,771,713 (Roberts); 4,715,382 (Strand); 5,012, 810 (Strand et al.); and 5,133,356 (Bryan et al.), the disclosures of which are incorporated by reference herein.

In those electrodes that also employ border areas of a non-conductive biocompatible pressure sensitive adhesive, such border areas become optional with the use of polymerized microemulsion PSA's of the present invention. Desirably, such border areas can be eliminated because it is no longer necessary.

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snap-type connector such as that disclosed in U.S. Pat. No. 4,846,185. Further, the means for electrical communication can be a lead wire such as that seen in U.S. Pat. No. 4,771,783. Regardless of the type of means for electrical communication employed, a polymerized microemulsion PSA of the present invention, containing an electrolyte, can reside as a field of conductive adhesive on a biomedical electrode for diagnostic (including monitoring), therapeutic, or electrosurgical purposes.

Another type of diagnostic procedure which can employ a biomedical electrode of the present invention is the longer term monitoring of electrical wave patterns of the heart of a patient to detect patterns of abnormality. A preferred biomedical electrode structure is disclosed in U.S. Pat. No. 5,012,810 (Strand et al.) which is incorporated by reference. The polymerized microemulsion PSA of the present invention can be used as the ionically conductive medium in any of the embodiments shown therein. Preferably, the polymerized microemulsion PSA of the present invention is used as the field of conductive adhesive in the biomedical electrode of the embodiment shown in FIGS. 2, 3, and 4 of U.S. Pat. No. 5,012,810.

FIGS. 7 and 8 substantially correspond to FIGS. 2 and 3, respectively, of U.S. Pat. No. 5,012,810. Electrode 40 includes an insulator construction 41, and a conductor member 42.

The insulator construction 41 includes first and second sections 44 and 45 which, together, define opposite sides 46 and 47 of the insulator construction 41. As seen in FIG. 7, each section 44 and 45 includes an elongate edge portion 50 and 51, respectively. The edge portions 50 and 51 each include a border portion 52 and 53, respectively, which comprise a peripheral portion of each section 44 and 45, respectively, and extending along edges 50 and 51, respectively. In that manner, sections 44 and 45 are oriented to extend substantially parallel to one another, with edge portions 50 and 51 overlapping one another such that border portions 52 and 53 overlap. A seam 60 is created between edge portions 50 and 51. "Substantially parallel" does not mean that the sections 44 and 45 are necessarily precisely parallel. They may be out of precise coplanar alignment due, for example, to the thickness of the conductor member 42.

Conductor member 42 is substantially similar to biomedical electrical conductor 16 described above, having a tab portion 61 corresponding to tab portion 20 described above and a pad portion 62 corresponding to conductive interface portion 18 described above. Like biomedical electrical conductor member 16, conductor member 42 can be any of the embodiments disclosed above. In this embodiment conductor member 42 is a multi-layered construction of a nonconductive, flexible organic polymer substrate 63 having an organosulfur surface 64, a metallic layer 65 adhered thereto, and, optionally, a metallic halide layer 66, produced according to the disclosure of U.S. patent application Ser. No. 08/063,960 described above.

The pad portion 62 of member 42 comprises the portion of the metallic film facing field 70 of conductive adhesive, optionally with metallic halide layer 66 contacting field 70. Because depolarizing is not needed for the mechanical and electrical contact with electrical equipment, metallic halide layer 66 need not extend to tab portion 61. Optionally, an adhesively-backed polyethylene tape can be applied to tab portion 61 in the same manner as that for the embodiment of FIGS. 5 and 6 in order to enhance mechanical contact.

In general, electrode 40 is constructed such that tab portion 61 of conductor member 42 projects through seam 60 and over a portion of surface or side 46. As a result, as seen in FIGS. 7 and 8 pad portion 62 of conductor member 42 is positioned on one side 47 of insulator construction 41, and the tab portion 61 of conductor member 42 is positioned on an opposite side 46 of insulator construction 41. It will be understood that except where tab portion 61 extends through seam 60, the seam may be sealed by means of an adhesive or the like.

As seen in FIG. 8, lower surface 68 of tab portion 61 is shown adhered in position to section 45, by means of double-stick tape strip 69. That is, adhesion in FIG. 5 between the tab portion 61 and section 45 is by means of adhesive 69 underneath tab portion 61, rather than on top as shown in FIG. 4.

In FIG. 8, a field 70 of conductive adhesive of polymerized microemulsion PSA of the present invention is shown positioned generally underneath conductive member 42. Optionally, field 70 of conductive adhesive will be surrounded by a field 71 of biocompatible skin adhesive also applied to insulator construction 41 the side thereof having pad portion 62 thereon. However, because of the hydrophobic pressure sensitive adhesive bulk properties of the polymerized microemulsion PSA of the present invention, field 71 can be eliminated or can be also the polymerized microemulsion PSA of the present invention.

In FIG. 8, a layer of release liner 75 is shown positioned against that side of electrode 40 which has optional skin adhesive 71, conductive adhesive 70 and pad portion 62 thereon. Optionally as shown in FIG. 8, a spacer 76 or tab 76 can be positioned between release liner 75 and a portion of insulator construction 41, to facilitate the separation.

A variety of release liners 75 may be utilized; for example, a liner comprising a polymer such as a polyester or polypropylene material, coated with a silicone release type coating which is readily separable from the skin adhesive and conductive adhesive.

A variety of materials may be utilized to form the sections 44 and 45 of the insulator construction 41. In general, a flexible material is preferred which will be comfortable to the user, and is relatively strong and thin. Preferred materials are polymer foams, especially polyethylene foams, nonwoven pads, especially polyester non-wovens, various types of paper, and transparent films. Nonlimiting examples of transparent films include polyester film such as a polyester film commercially available as "Melinex" polyester film from ICI Americas, Hopewell, Va. having a thickness of 0.05 mm and a surgical tape commercially available from 3M Company as "Transpore" unembossed tape.

The most preferred materials are non-woven pads made from melt blown polyurethane fibre, which exhibit exceptional flexibility, stretch recovery and breathability. Melt blown polyurethane materials usable in insulator construction 41 in electrodes according to the present invention are generally described in European Patent Publication 0 341 875 (Meyer) and corresponding U.S. Pat. No. 5,230,701 (Meyer et al.), incorporated herein by reference.

Optionally the insulator construction has a skin adhesive on its surface contacting the remainder of the electrode 40.

Preferred web materials (melt blown polyurethanes) for use in insulator construction 41 have a web basis weight of about 60–140 g/m$^2$ (preferably about 120 g/m$^2$). Such materials have an appropriate tensile strength and moisture vapor transmission rate. A preferred moisture vapor transmission rate is about 500–3000 grams water/m$^2$/24 hours (preferably 500–1500 grams water/m$^2$/24 hours) when tested according to ASTM E96-80 at 21° C. and 50% relative humidity. An advantage to such materials is that webs formed from them can be made which exhibit good elasticity and stretch recovery. This means that the electrode can stretch well, in all directions, with movement of the subject, without loss of electrode integrity and/or failure of the seal provided by the skin adhesive. Material with a stretch recovery of at least about 85%, in all directions, after stretch of 50% is preferred.

It will be understood that a variety of dimensions may be utilized for the biomedical electrode disclosed herein. Generally an insulator construction of about 3.5–4.5 cm by 5.5–10 cm will be quite suitable for typical foreseen applications. A thickness of about 200 to 600 $\mu$m provides for adequate strength and a desired low relief or profile, in typical applications.

It will also be understood that a variety of materials may be utilized as the skin adhesive, if polymerized microemulsion PSA is not employed or if the field 71 is not eliminated. Typically, acrylate ester adhesives will be preferred. Acrylate ester copolymer adhesives are particularly preferred. Such material are generally described in U.S. Pat. Nos. 2,973,826; Re 24,906; Re 33,353; 3,389,827; 4,112,213; 4,310,509; 4,323,557; 4,732,808; 4,917,928; 4,917,929; and European Patent Publication 0 051 935, all incorporated herein by reference.

In particular, an adhesive copolymer having from about 95 to about 97 weight percent isooctyl acrylate and from about 5 to about 3 percent acrylamide and having an inherent viscosity of 1.1–1.25 dl/g is presently preferred.

Adhesive useful as for adhesive 69 can be any of the acrylate ester adhesives described above in double stick tape form. A presently preferred adhesive is the same adhesive as presently preferred for the skin adhesive except having an inherent viscosity of about 1.3–1.45 dl/g.

For the field 70 of conductive adhesive, conductive adhesives such as those described above as useful for field 14 of conductive medium are preferred.

It will be understood that the dimensions of the various layers, and their conformation during association, are shown somewhat exaggerated in FIG. 8, to facilitate an understanding of the construction. In general, an overall substantially flat appearance with only a very minor "s" type bend in the conductive member 42 is accommodated by the arrangement, despite the multilayered construction of member 42.

Figure 9:
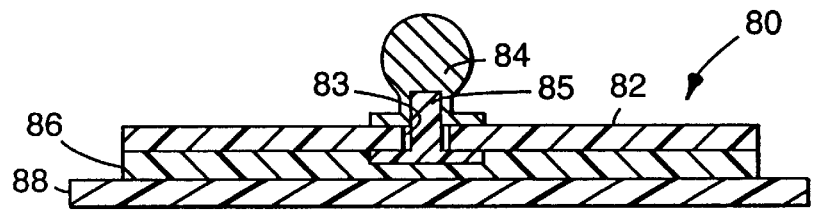
FIG. 9 is a cross-sectional view of another monitoring biomedical electrode containing a polymerized microemulsion PSA of the present invention and a stud connector.

Another biomedical electrode construction is shown in FIG. 9 in cross-section. Electrode 80 has a nonconductive backing 82 having an opening 83 covered by snap 84 though which stud or eyelet 85 protrudes. The snap 84 is secured to eyelet 85 to provide a point of electrical connection to electrical instrumentation. Covering eyelet 84 and backing 82 is a field 86 of the polymerized microemulsion PSA of the present invention. A release liner 88 protects the PSA field 86 prior to use. Backing 82 can be made of the same or similar materials as insulator construction 41. Eyelet 85 can be a plastic, metallic plated eyelet (such as an ABS plastic eyelet silver-plated and chlorided and commercially available from Micron Products of Fitchburg, Mass.). Snap 84 can be a metallic snap (such as stainless steel eyelet No. 304 commercially available from Eyelets for Industry of Thomason, Conn.). Electrode 80 is particularly preferred because the polymerized microemulsion PSA of the present invention can serve both as the biocompatible skin adhesive and as the ionically conductive medium in the electrode 80. By comparison, a monitoring electrode that requires a skirt of biocompatible skin adhesive to surround a nonadhesive but ionically conductive gel pad, such as a Red Dot™ brand electrode commercially available from Minnesota Mining and Manufacturing Company is a more complicated construction.

Other examples of biomedical electrodes which can use the present invention as a conductive adhesive include electrodes disclosed in U.S. Pat. No. 4,527,087; 4,539,996; 4,554,924; 4,848,353 (all Engel); 4,846,185 (Carim); 4,771,713 (Roberts); 4,715,382 (Strand); 5,133,356 (Bryan et al.), the disclosures of which are incorporated by reference herein. Methods of making such electrodes are disclosed in such patents, except that polymerized microemulsion PSA of the present invention can be substituted for the field of conductive adhesive and optionally also the field of skin adhesive disclosed in such patents. Among these various electrode constructions is an electrode construction particularly preferred as that shown in FIGS. 4 and 5 of U.S. Pat. No. 4,848,353 (Engel) in which the electrically conductive adhesive 36 is replaced by the polymerized microemulsion PSA of the present invention, and in which the biocompatible PSA 32 is optionally eliminated or optionally replaced by the polymerized microemulsion PSA of the present invention.

When used for diagnostic EKG procedures, electrodes shown in FIGS. 5 and 6 or those electrodes shown in U.S. Pat. No. 4,539,996 are preferred. When used for monitoring electrocardiogram (ECG) procedures, electrodes shown in FIGS. 7 and 8 and those disclosed in U.S. Pat. Nos. 4,539,996, 4,848,353, 5,012,810 and 5,133,356 are preferred.

In some instances, the biomedical electrical conductor can be an electrically conductive tab extending from the periphery of the biomedical electrodes such as that seen in U.S. Pat. No. 4,848,353 or can be a conductor member extending through a slit or seam in a insulating backing member, such as that seen in U.S. Pat. No. 5,012,810. Otherwise, the means for electrical communication can be an eyelet or other snap-type connector such as that disclosed in U.S. Pat. No. 4,846,185. Alternatively, an electrically conductive tab such as that seen in U.S. Pat. No. 5,012,810 can have an eyelet or other snap-type connector secured thereto.

Medical Skin Coverings

Medical skin coverings employing polymerized microemulsion PSA's of the present invention, optionally having antimicrobial and other biologically active agents contained therein, are useful for treatment of mammalian skin or mammalian skin openings, preferably against the possibility of infection and also for the transmission of moisture vapor and exudate from skin.

Figure 10:
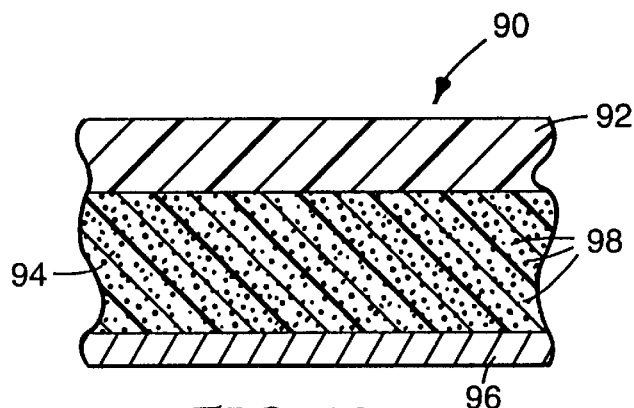
FIG. 10 is a sectional view of a medical mammalian skin covering containing polymerized microemulsion PSA of the present invention.

FIG. 10 shows a sectional view of a medical skin covering 90 having a backing material 92, a layer 94 of polymerized microemulsion PSA of the present invention coated on backing material 92, and protected until use by a release liner 96. Preferably, antimicrobial 98 is contained in layer 94 by adding agent 98 prior to coating on backing material 92. Alternatively, layer 94 can be used as a caulkable sealant according to U.S. Pat. No. 4,931,282 (Asmus et al.), the disclosure of which is incorporated by reference herein.

For use, the release liner 96 is removed and the layer 94 of polymerized microemulsion PSA can be applied to the skin of the patient as a part of a medical tape, a wound dressing, a bandage of general medicinal utility, or other medical device having water moisture absorbing properties.

The adhesive layer 94 may be coated on a layer of backing material 92 selected from any of several backing materials having a high moisture vapor transmission rate for use as medical tapes, dressings, bandages, and the like. Suitable backing materials include those disclosed in U.S. Pat. Nos. 3,645,835 and 4,595,001, the disclosures of which are incorporated by reference. Other examples of a variety of films commercially available as extrudable polymers include "Hytrel® 4056" and "Hytrel® 3548" branded polyester elastomers available from E.I. DuPont de Nemours and Company of Wilmington, Del., "Estane" branded polyurethanes available from B.F. Goodrich of Cleveland, Ohio or "Q-thane" branded polyurethanes available from K. J. Quinn & Co. of Malden, Mass.

The layer 94 of polymerized microemulsion PSA combined with a layer 92 of suitable backing material can be used as a dressing.

Polymerized microemulsion PSA's of the present invention have excellent moisture vapor transmission properties. Moist vapor transmission rates of adhesive layer 94 approach (i.e., within 80%) and sometimes exceed the moisture vapor transmission rate of backing layer 92, such that moisture vapor and body exudate can be readily transmitted from mammalian skin.

Polymerized microemulsion PSA's of the present invention can be used as discrete gel particles dispersed in a continuous pressure-sensitive adhesive matrix to form a two phase composite useful in medical applications, as described in U.S. Pat. No. 5,270,358, the disclosure of which is incorporated by reference herein.

The adhesive layer 94 can be coated on the backing layer 92 by a variety of processes, including, direct coating, lamination, and hot lamination. The release liner 96 can thereafter be applied using direct coating, lamination, and hot lamination.

The methods of lamination and hot lamination involve the application of pressure, or heat and pressure, respectively, on the layer of adhesive layer 94 to the backing material layer 92. The temperature for hot lamination ranges from about 50° C. to about 250° C., and the pressures applied to both lamination and hot lamination range from 0.1 Kg/cm$^2$ to about 50 Kg/cm$^2$.

Pharmaceutical Delivery Devices

Pharmaceutical delivery devices employing hydrophilic, pressure-sensitive adhesive compositions of the present invention, optionally having a topical, transdermal, or iontophoretic therapeutic agent and excipients, solvents, or penetration enhancing agents contained therein, are useful for delivery of pharmaceuticals or other active agents to or through mammalian skin.

Figure 11:
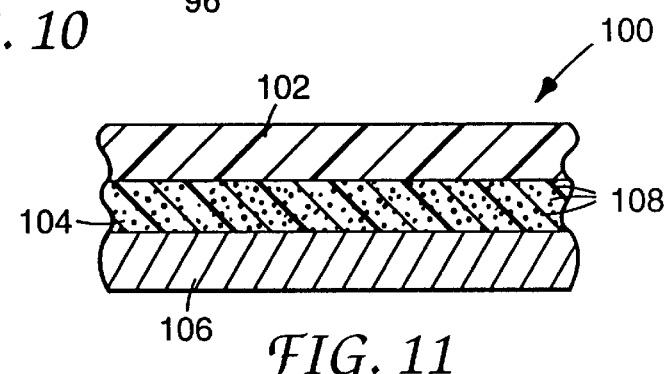
FIG. 11 is a sectional view of a pharmaceutical delivery device containing a polymerized microemulsion PSA of the present invention.

FIG. 11 shows a sectional view of a transdermal or topical drug delivery device 100 having a backing layer 102, a layer 104 containing polymerized microemulsion PSA of the present invention coated thereon and protected by a release liner 106. Other layers can be present between layer 102 and layer 104 to house pharmaceuticals or other therapeutic agents. Otherwise, as shown in FIG. 11, pharmaceutical and other agents 108 are dispersed in adhesive layer 104.

The backing layer 102 can be any backing material known to those skilled in the art and useful for drug delivery devices. Non-limiting examples of such backing materials are polyethylene, ethylene-vinyl acetate copolymer, polyethylene-aluminum-polyethylene composites, and "ScotchPak™" brand backings commercially available from Minnesota Mining and Manufacturing Company of St. Paul, Minn. (3M).

The release liner 106 can be any release liner material known to those skilled in the art. Non-limiting examples of such release liners commercially available include siliconized polyethylene terephthalate films commercially available from H. P. Smith Co. and fluoropolymer coated polyester films commercially available from 3M under the brand "ScotchPAk™" release liners.

The therapeutic agent 108 can be any therapeutically active material known to those skilled in the art and approved for delivery topically to or transdermally or iontophoretically through the skin of a patient. Non-limiting examples of therapeutic agents useful in transdermal delivery devices are any active drug or salts of those drugs, used in topical or transdermal applications, or growth factors for use in enhancing wound healing. Other therapeutic agents identified as drugs or pharmacologically active agents are disclosed in U.S. Pat. Nos. 4,849,224 and 4,855,294, and PCT Patent Publication WO 89/07951.

Excipients or penetration enhancing agents are also known to those skilled in the art. Non-limiting examples of penetration enhancing agents include ethanol, methyl laurate, oleic acid, isopropyl myristate, and glycerol monolaurate. Other penetration enhancing agents known to those skilled in the art are disclosed in U.S. Pat. Nos. 4,849,224; and 4,855,294 and PCT Patent Publication WO 89/07951.

The method of manufacturing a transdermal delivery device depends on its construction.

The drug delivery device 100 shown in FIG. 11 can be prepared using the following general method. A solution is prepared by dissolving the therapeutic agent 108 and such optional excipients as are desired in a suitable solvent and mixed into the microemulsion prior to forming the composition, during the formation of the composition, or directly into the already formed composition. The resulting loaded adhesive composition is coated on the backing layer 102. A release liner 106 is applied to cover loaded adhesive layer 104.

Industrial Usage

Polymerized microemulsion PSA's of the present invention can have use in industrial environments where a continuous pressure sensitive adhesiveness and ionic conductivity are desired.

Nonlimiting examples of industrial uses include antistatic adhesives, conductive tapes, and the like.

Of these examples, one desired usage is for cathodic protection of galvanically active metals, such as metallic reinforcing bars embedded in concrete that are susceptible to corrosion.

The polymerized microemulsion PSA can serve as a pressure sensitive adhesive laminated to a zinc plate that forms a galvanic circuit with iron reinforcing bars embedded in concrete when the pressure sensitive adhesive contacts the concrete and when the plate and the bars are connected electrically. The flow of ions, caused by dissolution of zinc from the plate functioning as a sacrificial anode, through the adhesive and into the concrete minimizes corrosion of the reinforcing bars embedded in the concrete.

Copending, coassigned U.S. patent application Ser. No. 08/189,443 (Huang et al.), the disclosure of which is incorporated by reference herein, describes an ionically-conductive interface for galvanically active metals used in electrochemical reactions comprising an idoicallyconductive medium and a means associated with that medium for reducing passivation of metal subject to anodic dissolution. Polymerized microemulsion PSA's of the present invention are suitable as the ionically-conductive medium.

In a preferred embodiment disclosed in Huang et al., the polymerized microemulsion PSA has included therein a means for reducing passivation of metal subject to anodic dissolution.

In one aspect of this embodiment, the means for controlling transfer of ions through the ionically conductive medium employs an ion selective membrane that inhibits transfer of OH$^-$ or H$^+$ ions that would otherwise alter the pH of the ionically conductive medium.

In another aspect of this embodiment, the means for controlling transfer of ions through the ionically conductive medium employs a complexing agent to facilitate continued dissolution of metal to avoid precipitation of metallic hydroxides that would otherwise form a passivation layer at or near the metal contacting the ionically conductive medium. Of these two aspects, the complexing agent is preferred.

Figure 12:
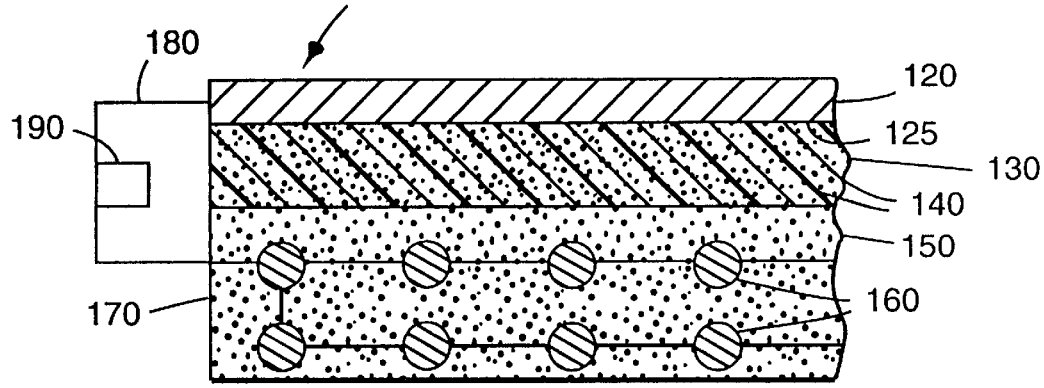
FIG. 12 is a sectional view of a system for cathodic protection of reinforcing bars in concrete using a polymerized microemulsion PSA of the present invention.

FIG. 12 shows a system 110 for cathodic protection of reinforced concrete. System 110 comprises a layer of zinc 120 having a thickness of from about 0.1 mm to about 0.5 mm and having a 18 gage. Sacrificial layer 120 contacts a field 130 of polymerized microemulsion PSA having dispersed or dissolved therein, a complexing agent 140. Field 130 of PSA contacts concrete 150 having embedded therein an array of reinforcing bars 160 mechanically connected emerging from end 170 is an electrical connection 180 that electrically connects reinforcement bars 160 to sacrificial layer 120. A galvanic circuit is created from bars 160 through connection 180 to layer 120, which is completed by the migration of zinc ions from layer 120 toward reinforcing bars 160. Without the presence of complexing agent 140, zinc hydroxide forms at or near surface 125 of layer 120 contacting PSA 130. After continuous formation of zinc hydroxide at or near surface 125, the galvanic circuit will cease functioning prior to exhaustion of layer 120 designed to preserve bars 160 from the effects of corrosion.

Optionally, to enhance the protection of rebars in concrete of low conductivity, electrical power supply 190 can be introduced to connection 180 between bars 160 and layer 120 to provide better conductivity for the concrete in the galvanic circuit. Low conductivity is present in colder, dryer climates. Concrete structures in these colder, dryer climates nonetheless require protection from corrosion caused by salt spray on highways, in parking decks and the like. Cathodic protection in warmer, more humid climates may not need optional power supply 190 but is equally useful for bridges, balconies and other concrete structures that are exposed to humid, warm environments, particularly near sea water.

Complexing agents useful in the ionically conductive interface of the present invention are those complexing agents which are capable of intimately dispersing or otherwise dissolving into the ionically conductive medium in a manner that reduces passivation of metal subject to anodic dissolution. Some complexing agents are of a suitable size that permits multiple complexing of multiple portions of the complexing agent with the same metallic ion. Other complexing agents provide a single complexing site for galvanically active metal ion.

When the galvanically active metal is zinc, the complexing agents can be selected from the group consisting of molecular complexing agents that are free for diffusion and polymeric complexing agents that remain in the ionically conductive medium.

Nonlimiting examples of smaller complexing agents are ethylenediamine tetraacetic acid and its salts (collectively "EDTA"), cyanide compounds such as NaCN and KCN, and thiocyanate compounds such as NaSCN and KSCN.

Nonlimiting examples of polymeric complexing agents are poly(vinyl amines), poly(allyl amines), poly(alkylene amines), poly(ethylenimine)("PEI"), poly(vinyl pyridines), poly(vinyl pyrroles), poly(N-vinyl lactams) and poly (alkylene oxides).

Of these transport complexing agents, PEI is presently preferred due to its commercial availability, its low cost, its complexing in a pH range compatible with the pH of reinforced concrete structures, its complexing availability in an aqueous solution form, its nonreactivity with the preferred hydrophilic pressure sensitive adhesives used in the ionically conductive medium, and its electrochemical stability throughout completion of the galvanic circuit duration.

Complexing agents can be added to the ionically conductive medium in any effective weight percent to serve as a complexing agent for a dissolved metal, and desirably in a weight percent ranging from about 1 to about 15 weight percent of the ionically conductive medium. Preferably, such weight range ranges from about 3 to about 6 weight percent.

As described above, the complexing agent reduces passivation of the sacrificial metal by stabilizing such metallic ions as dissolution of the metal occurs. Such stabilization includes both solubilizing of the metallic ions and the inhibition of the formation of a passivation layer near the surface of the sacrificial metal.

Preferred Substantially Nonporous, Bicontinuous Structure

Polymerized microemulsion PSA's of the present invention preferably have a substantially nonporous, bicontinuous structure.

Test Methods

Skin Adhesion Test

Strips of polymerized microemulsion PSA laminated on polyester film were cut to have dimensions of about 2.54 cm×7.6 cm. The strips were applied on the backs of human subjects perpendicular to the backbone and rolled with a 2 kg roller to insure uniform application. The strips were removed promptly after application from the back using a mechanical pulling device termed an adhesion tester. This device consists of a motor driven screw drive which pulls a 11.4 kg test line to which is attached a metal clip which is 2.54 cm wide. The metal clip is attached to each stip at its 2.54 cm width during pulling testing. Strips were pulled in a plane parallel (180°) to the back and parallel to the long axis of the strip at a rate of 13–14 cm/min. The adhesion is reported in grams/2.54 cm and based on an average of values from initiation of peel to entire removal of the electrode.

Skin and Back-to-Back Alternating Current Impedance Tests

Skin impedance was measured using a 4800A Vector Impedance Meter manufactured by Hewlett Packard of Palo Alto Calif. on human arms. Biomedical electrodes were placed on the panelists' arms and measured for alternating current impedance in kOhms at a frequency of 10 Hz. Biomedical electrodes (Red Dot ™ Brand Model 2259 biomedical electrodes commercially available from 3M, St. Paul, Minn.) were used as the reference electrodes.

Alternating current impedance was measured using an Xtratek ET-65A ECG Electrode Tester from Xtratek Company of Lenexa, Kans. Measurements were conducted in the conventional manner on electrode pairs connected "back-to-back" (adhesive-to-adhesive) using a low level signal suitable for measurements on ECG electrodes. The impedance at 10 Hz was recorded.

The Association for the Advancement of Medical Instrumentation (AAMI) has adopted the following standards and testing methods to determine proper performance for a biomedical electrode used for ECG Disposable Electrodes. See the "American National Standard for Pregelled ECG Disposable Electrodes" Association for the Advancement of Medical Instrumentation (1984), the disclosure of which is incorporated by reference, for testing methods and conditions for minimum standards for D.C. Offset (100 mV), A.C. Impedance (2 kOhms), and Defibrillation Overload Recovery (less than 100 mV 5 seconds after 4 capacitor discharges and a rate of change of residual polarization potential no greater than 1 mV/sec.) Less than about 500 kOhms has been found acceptable for human skin impedance.

PSTC-1 Test

Polymer compositions were tested according to PSTC-1 (11/75) Test and further described in U.S. Pat. Nos. 4,952, 650 (Young et al.) or 4,833,179 (Young et al.) (both incorporated by reference herein) for pressure sensitive adhesive properties by coating 10 mil (0.254 mm) thick field of the polymer composition on a 15.24 cm (6 inch) wide, 1.5 mil (0.038 mm) thick polyethylene terephthalate film. From this coated film, two test strips (each being 12.5 mm (½ inch) wide and about 30 cm long) for each Example tested were prepared for wet adhesion and two test strips (each being 12.5 mm (½ inch) wide and about 30 cm long) for each Example tested were prepared for dry adhesion.

Each coated test strip was applied to the horizontal surface of a clean glass test plate with at least 12.7 lineal cm in firm contact. A hard rubber roller was used to apply this strip. The free end of each coated strip was doubled back nearly touching itself, so the angle of removal was 180°. The free end was attached to the adhesion tester scale.

The glass test plate was clamped in the jaws of the tensile testing machine (Peel Adhesion Tester Model SP-102C made by IMASS Inc. for the PSTC-1 Test) which was capable of moving the plate away from the scale at a constant rate of 2.3 meters per minute. The scale reading in ounces was recorded as the tape was peeled from the glass surface. The data was recorded as the average value of the range of numbers observed during the peeling test. The value in ounces per ½ inch was converted and normalized to Newtons/100 mm

Abbreviations and Tradenames

The following abbreviations and tradenames are used herein:

| | |
|---|---|
| Comp. | Comparative |
| DI water | Deionized water |
| IBOA | Isobornyl acryalte |
| IOA | Isooctyl acrylate |
| BA | Butyl acrylate |
| AMPS | 2-acrylamido-2-methyl propane sulfonic acid (Solution 2405 (a 50% aqueous solution, sodium salt) from Lubrizol, Inc. of Wickliffe, OH) |
| AA | Acrylic acid |
| MAA | Methacrylic acid |
| NVP | N-vinyl pyrrolidone |
| AcM | Acrylamide |
| NAcM | N,N-dimethylacrylamide |
| SAM 211 | Alkylene polyalkoxy sulfate surfactant under the Mazon ™ brand from PPG Industires, Inc. |
| PI | 2,2-dimethyl-2-phenyl-acetophenone photoinitiator, from Sartomer Chemicals or Ciba Giegy |
| KCl | Potassium chloride |
| LiCl | Lithium chloride |
| CA750 | Poly(ethylene oxide) acrylate also called poly(oxyethylene) acrylate (750 molecular weight) |
| AM90G Ester | Poly(ethylene oxide) acrylate from polyfunctional monomer available from Shin-Nakamura Chemical Co. Ltd. of Wakayama, Japan |
| PEG400 | Poly(ethylene glycol) diacrylate (400 M.W.) from Sartomer Chemical Co. |
| M.W. | Molecular weight |
| Tergitol 15-S-12 | Ethoxylated fatty alcohol surfactant available from Sigma Chemicals |
| SDS | Sodium dodecyl sulfate surfactant available from Sigma Chemicals |
| DS | Dioctyl sulfosuccinate, sodium salt, available from Sigma Chemicals |
| Brij ™76 | Polyoxyethylene 10 stearyl ether available from Sigma Chemicals |
| Brij ™96 | Polyoxyethylene 10 oleyl ether available from Sigma Chemicals |

EXAMPLES

The following examples further illustrate but do not limit the present invention. Unless otherwise indicated, all values are in grams. Chemicals were used without further purification.

Examples 1–7

Examples 1–7 were prepared with Brij™ 76 surfactant and varying amounts of AA, AM90G Ester, and IOA. These samples are represented in the phase diagram shown in FIG. 2 and the formulations are listed in Table 1. The solutions were prepared by addition of AA and AM90G Ester (in a 70/30 AA/AM90G Ester weight ratio in the First Mixture as described above) to IOA (in various weight ratios in the Second Mixture). The photoinitiator, PI, (in various weight ratios in the Third Mixture) was then dissolved in the resultant solution followed by the addition of the Brij™ 76 surfactant (in a 15/85 Surfactant/Total Monomers and Initiator weight ratio in the Fourth Mixture), and then followed by the approximately 4% aqueous KCl solution (in various weight ratios in the Microemulsion). Each of Examples 1–7 are located within the shaded microemulsion area of the phase diagram of FIG. 2, as indicated by the points shown in FIG. 2. The resultant microemulsion solutions were then cast in a 0.38 mm thickness onto a silicone treated paper substrate (polyethylene coated, moisture resistant Kraft paper #56) and covered with a silicone treated transparent polyester film about 0.05 mm thick. The cast microemulsion was photopolymerized in air, (ambient temperature, pressure, and humidity) using a black light (Model F15TB/350BL consuming 15 Watts of power and commercially available from Sylvania) emitting light at about 351 nm for a time sufficient to achieve about 680 milliJoules/cm$^2$ of energy/area of cast microemulsion, to assure complete photopolymerization. About 10 minutes was needed to complete photopolymerization in each instance.

TABLE 1

| # | AA | AM90G Ester | IOA | PI | Brij 76 | Water | KCl |
|---|---|---|---|---|---|---|---|
| 1 | 0.87 | 2.03 | 1.25 | 0.02 | 0.73 | 0.83 | 0.04 |
| 2 | 1.01 | 2.36 | 0.84 | 0.02 | 0.73 | 0.84 | 0.04 |
| 3 | 2.23 | 5.2 | 7.25 | 0.08 | 2.54 | 2.70 | 0.11 |
| 4 | 2.19 | 5.12 | 1.89 | 0.08 | 1.63 | 8.82 | 0.37 |
| 5 | 1.22 | 2.86 | 2.72 | 0.04 | 1.20 | 1.69 | 0.07 |
| 6 | 1.19 | 2.77 | 2.13 | 0.04 | 1.08 | 1.72 | 0.07 |
| 7 | 1.20 | 2.80 | 1.71 | 0.04 | 1.01 | 2.15 | 0.09 |

Electrodes were constructed by laminating a 2.54 cm×1.9 cm piece of the polymerized microemulsion PSA onto a 3.17 cm×1.9 cm polyester film having a Ag/AgCl ink commercially available as Ercon R300 ink from Ercon, Inc. of Waltham, Mass., in the manner of an electrode shown in FIGS. 5 and 6. The metallic film extended 0.63 cm beyond the PSA field to provide a tab for electrical and mechanical contact with the Xtratek Electrode Tester. Alternating impedance in accordance with AAMI standards were measured for electrodes made from adhesives from Examples 5–7. Alternating current impedance was measured to be 235 ohms, 175 ohms, and 140 ohms, respectively. The polymerized microemulsion PSA of the present invention provided both excellent adhesion and excellent ionic conductivity, indicative of both a hydrophobic PSA bulk property and a hydrophilic conductive polymer bulk property.

Examples 8–13

Another set of examples was prepared in which the First Mixture described above consisted of NVP and AM90G in a 30/70 weight ratio. Samples were prepared and photopolymerized as in Examples 1–7. The surfactant was changed to SAM211. The complete formulations are listed in Table 2.

TABLE 2

| # | NVP | AM90G Ester | IOA | PI | SAM211 | Water | KCl |
|---|---|---|---|---|---|---|---|
| 8 | 0.84 | 1.97 | 2.81 | 0.03 | 0.99 | 0.56 | 0.02 |
| 9 | 0.53 | 1.24 | 2.65 | 0.02 | 0.73 | 0.54 | 0.02 |
| 10 | 0.80 | 1.87 | 1.78 | 0.02 | 0.79 | 0.55 | 0.02 |
| 11 | 0.80 | 1.87 | 1.78 | 0.02 | 0.79 | 0.98 | 0.04 |
| 12 | 1.29 | 3.0 | 1.84 | 0.03 | 1.10 | 0.76 | 0.03 |
| 13 | 1.29 | 3.0 | 1.84 | 0.03 | 1.10 | 1.33 | 0.05 |

Alternating current impedance tests were performed in the manner of Examples 1–7 for the adhesives of Examples 11 and 13 using electrodes conducted according to Examples 1–7. The impedances were 290 ohms and 238 ohms, respectively. This set of Examples 8–13 shows a variety of polymerized microemulsion PSA's can be made using different hydrophilic components and surfactants without detracting from the excellent bulk pressure sensitive adhesive properties or the the excellent bulk ionic conductivity properties.

Examples 14–19

Another series of examples was prepared in which the ratio of AA to CA750 was varied from 15:85 to 40:60. The amounts of IOA, SAM211 and water were fixed and comparative samples were prepared with LiCl vs. KCl. Microemulsions were prepared and photopolymerized in the manner according to Examples 1–7. The exact formulations are shown below in Table 3. All of the formulations contained 0.8 g of PI.

TABLE 3

| #  | AA   | CA750 | IOA | SAM 211 | Water | LiCl | KCl  | Skin Z kOhms |
|----|------|-------|-----|---------|-------|------|------|--------------|
| 14 | 4.56 | 24.62 | 46  | 16      | 8.36  | 0.46 | 0    | 150          |
| 15 | 6.84 | 22.34 | 46  | 16      | 8.36  | 0.46 | 0    | 240          |
| 16 | 9.12 | 20.06 | 46  | 16      | 8.36  | 0.46 | 0    | 190          |
| 17 | 11.4 | 17.78 | 46  | 16      | 8.36  | 0.46 | 0    | 160          |
| 18 | 6.84 | 22.34 | 46  | 16      | 8.36  | 0    | 0.46 | 140          |
| 19 | 9.12 | 20.06 | 46  | 16      | 8.36  | 0    | 0.46 | 180          |

As seen in Table 3, skin impedance (Skin Z) was measured using electrodes made according to Examples 1–7. Skin impedance was determined against a Red Dot™ Brand Model 2259 biomedical electrode (commercially available from Minnesota Mining and Manufacturing Company of St. Paul, Minn.) with abrasion of the skin as a reference. Skin impedance for all electrodes were within acceptable limits. Examples 14–19 demonstrate excellent bulk pressure sensitive adhesive properties and excellent skin impedance properties with other microemulsion formulations that vary electrolyte from KCl to LiCl and amphiphilic oligomer from AM90G to CA750, as compared with Examples 1–7.

Example 20

A First Mixture was prepared in which 12.31 g AA was charged with 25.20 g of CA750. To this First Mixture 71.25 g of IOA was added to form a Second Mixture and then 0.8 g of PI was added to form a Third Mixture. Then 24.99 g of SAM211 was added to form a Fourth Mixture. The Fourth Mixture was mixed on a vortex mixer for 5 minutes to dissolve the PI. Then 16.6 g of an aqueous 4% KCl solution was added to the Fourth Mixture, and upon further mixing, a translucent microemulsion was obtained. The sample was photopolymerized as described in Examples 1–7 at a thickness of 0.38 mm. Biomedical electrodes were prepared in a center style stud design, comprising a stud, a backing, and the polymerized microemulsion PSA as shown in FIG. 9. The polymerized microemulsion PSA was the only source of adhesion for the test electrodes on skin for test that simulate monitoring electrode conditions. The dimensions of the electrodes were 2.54 cm×3.49 cm. The electrodes were evaluated for skin impedance at t=0 and t=72 hours and long term wearability vs. Red Dot™ Brand Model 2259 biomedical electrode containing an outer skirt of nonconductive, biocompatible pressure sensitive adhesive in addition to a conductive gel pad. At t=0 hours, the average skin impedance of the electrodes containing the polymerized microemulsion PSA of Example 20 was 167 kOhms. After 72 hours, the skin impedance was 48 kOhms. By comparison, the average skin impedance of the 2271 electrodes were 130 kOhms and 30 kOhms at t=0 and t=72, respectively. Skin adhesion was at least as good using the test electrodes compared with the 2271 electrodes after 72 hours continuous skin contact. This comparison demonstrated that polymerized microemulsion PSA's have comparable ionic conductivity to a gel pad used in a commercially available biomedical electrode.

Also skin adhesion was determined against a two-phase composite as the pressure sensitive adhesive produced according to PCT Publication WO 93/07913 in a biomedical electrode in the shape of FIGS. 5 and 6 discussed above. After less than one day, the comparison electrode lost all skin adhesion and fell off of skin. This double comparison demonstrated that polymerized microemulsion PSA's of the present invention have comparable skin adhesion properties to a biocompatible skin adhesive employed on a commercially available electrode and superior skin adhesion properties to a two-phase composite where hydrophobic pressure sensitive adhesive is a dispersed phase.

Example 21

Another polymerized microemulsion PSA was prepared upon the photopolymerization according to Examples 1–7 of a microemulsion of 10.19 g AA, 23.78 g AM 90 G Ester, 14.89 g IOA, 0.31 of PI, 11.16 g SAM211, and 20.0 g of a 4% aqueous KCl solution. This Example falls within the shaded region of the phase diagram in FIG. 3. Electrodes were constructed similar to those described in Example 20, and the back to back impedance was determined to be 65 ohms. Skin adhesion was determined from the 180° peel test of a 2.54 cm×7.62 cm of the PSA coated on a polyester backing. The adhesion was 460 g/2.54 cm, an excellent adhesion value.

Example 22

Another polymerized microemulsion PSA was prepared upon the photopolymerization according to Examples 1–7 of a microemulsion of 8.66 g AA, 8.66 g AM 90 G Ester, 40.39 g IOA, 0.35 of PI, 12.67 g SAM211, and 16.08 g of a 4% aqueous KCl solution. Electrodes were constructed similar to described in Example 20 and back to back impedance was determined to be 62 ohms. Skin adhesion was determined from a 180° peel test of a 2.54 cm×7.62 cm strip of the PSA coated on a polyester backing. The adhesion was 462 g/2.54, an excellent adhesion value and comparable to the skin adhesion of Example 21 using a different microemulsion formulation.

Examples 23–27

A series of examples was prepared in which the level of photoinitiator was varied from 0.05% to 0.5%. Samples were prepared and polymerized as described in Examples 1–7. The formulations are listed in Table 4 below. The back to back alternating current impedance (ACZ) was measured according to AAMI standards, and the skin adhesion of these formulations was measured according to the test method used in Example 22 above. The results are listed in Table 5 and show both excellent bulk skin adhesion pressure sensitive adhesive properties and excellent ionic conductivity for polymerized microemulsion PSA's of a variety of photoinitiator amounts.

TABLE 4

| # | AA | CA750 | IOA | PI | SAM211 | Water | KCl |
|---|------|-------|------|-------|--------|-------|------|
| 23 | 0.47 | 2.44 | 4.65 | 0.005 | 1.56 | 0.83 | 0.05 |
| 24 | 0.47 | 2.44 | 4.65 | 0.010 | 1.56 | 0.83 | 0.05 |
| 25 | 0.47 | 2.44 | 4.65 | 0.020 | 1.56 | 0.83 | 0.05 |
| 26 | 0.47 | 2.44 | 4.65 | 0.040 | 1.56 | 0.83 | 0.05 |
| 27 | 0.47 | 2.44 | 4.65 | 0.050 | 1.56 | 0.83 | 0.05 |

TABLE 5

| # | AC Impedance (ohms) | Skin Adhesion (g/2.54 cm) |
|----|---------------------|---------------------------|
| 23 | 400 | 55 |
| 24 | 450 | 64 |
| 25 | 505 | 77 |
| 26 | 505 | 83 |
| 27 | 385 | 105 |

Example 28

A polymerized microemulsion PSA was prepared from the polymerization method according to Examples 1–7 of a inicroemulsion of 0.178 g AA, 0.267 g AM90G Ester, 0.658 g IOA, 0.003 g of PI, 0.194 g SAM211, and 0.096 g of a 4% aqueous KCl solution. The microemulsion represents a PSA polymerized from a microemulsion having a formulation within the shaded region in the phase diagram of FIG. 4.

Example 29

A polymerized microemulsion PSA was prepared from the polymerization method according to Examples 1–7 of a microemulsion of 3.05 g AA, 12.42 g NVP, 12.42 g CA750, 57.95 g IOA, 0.8 of PI, 0.194 g SAM211, and 5.16 g of a 7% aqueous KCl solution. The microemulsion was photopolymerized according to Examples 1–7 above and was evaluated for back to back impedance, yielding a value of 440 ohms.

Example 30

Another polymerized microemulsion PSA was prepared from the polymerization method according to Examples 1–7 of a microemulsion of 6.2 g AA, 24.75 g IOA, 0.4 g of PI, 12.85 g SAM211 and 6.30 g of an aqueous 4% KCl solution. Electrodes were prepared according to Examples 1–7, and the back to back impedance in the manner of Examples 1–7 was determined to be 55 ohms. This Example showed that an excellent polymerized microemulsion PSA can be prepared without the use of amphiphilic oligomer in the First Mixture.

Example 31

Another polymerized microemulsion PSA was prepared from the polymerization method according to Examples 1–7 of a microemulsion of 0.69 g AA, 5.06 g CA750, 9.84 g IOA, 2.52 g SAM211, 0.10 g of PI, 1.76 g of an aqueous 4% KCl solution and 0.13 g KOH. This example showed that an excellent polymerized microemulsion PSA can be prepared having a partially neutralized AA hydrophilic phase.

Example 32

A polymerized microemulsion PSA was prepared from the polymerization method according to Examples 1–7 of a microemulsion of 0.86 g AA, 5.0 g CA750, 0.04 g PEG400, 8.56 g IOA, 2.94 g SAM211, 0.10 g of PI, and 2.52 g of an aqueous 4% KCl solution.

Example 33

A polymerized microemulsion PSA was prepared from the polymerization method according to Examples 1–7 of a microemulsion of 9.00 g AA, 20.00 g of CA750, 23.0 g IOA, 23.0 g IBOA, 16.0 g SAM211, 0.8 g of PI, and 9.0 g of an aqueous 4% KCl solution. The back to back alternating current electrical impedance was determined for electrodes constructed according to Examples 1–7 with the resulting polymerized microemulsion PSA. The impedance was 900 ohms. This example showed a variation in hydrophobic monomers.

Example 34

A polymerized microemulsion PSA was prepared from the polymerization method according to Examples 1–7 of a microemulsion of 12.0 g MAA, 27.75 g CA750, 39.0 g IOA, 12.0 g SAM211, 0.8 g of PI, and 9.25 g of an aqueous 4% KCl solution. This example showed a variation in hydrophilic monomer.

Example 35

A polymerized microemulsion PSA was prepared,from the polymerization method according to Examples 1–7 of a microemulsion of 11.0 g AcM, 26.25 g CA750, 37.0 g IOA, 17.0 g SAM211, 0.50 g of PI, and 8.75 g of an aqueous 4% KCl solution. Skin impedance was determined according to Examples 14–19 for electrodes constructed according to Examples 1–7. The skin impedance was 85 kOhms. This Example demonstrated another polymerized microemulsion PSA with a different hydrophilic monomer.

Example 36

A polymerized microemulsion PSA was prepared from the polymerization method according to Examples 1–7 of a microemulsion of 0.86 g AA, 5.04 g AM90G, 8.56 g BA, 2.94 g SAM 211, 0.10 g of PI, and 2.52 g of 4% aqueous KCl solution. This Example demonstrated another polymerized microemulsion PSA with a different hydrophobic monomer.

Example 37

A polymerized microemulsion PSA was prepared from the polymerization method according to Examples 1–7 of a microemulsion of 12.0 g NAcM, 27.75 g CA750, 39.0 g IOA, 12.0 g SAM211, 0.5 g of PI, and 9.25 g of an aqueous 4% KCl solution. Skin impedance was determined according to Examples 14–19 for electrodes constructed according to Examples 1–7. The skin impedance was 40 kOhms. This Example demonstrated another polymerized microemulsion PSA with different hydrophilic components.

Example 38

A polymerized microemulsion PSA was prepared from the polymerization method according to Examples 1–7 of a microemulsion of 1.26 g AMPS, 0.22 g AM90G Ester, 0.22 NVP, 1.01 g IOA, 0.011 g of PI and 0.26 g SAM 211. This Example showed that a acrylate-containing, commercially available hydrophobic monomer can be used to construct a PSA of the present invention and that water in AMPS contributes to the formation of the microemulsion.

Example 39

A polymerized microemulsion PSA was prepared from the polymerization method according to Examples 1–7 of a microemulsion of 1.01 g AA, 2.35 g AM90G Ester, 0.84 g IOA, 0.02 g of PI, 0.74 g SDS, and 1.64 g of an aqueous 4% KCl solution. This example showed that a different surfactant can be used according to the present invention.

Example 40

A polymerized microemulsion PSA was prepared from the polymerization according to Examples 1–7 of a microemulsion of 0.686 g AA, 0.691 g CA750, 1.385 g IOA, 0.01 g of PI, 0.096 g Tergitol, and 0.140 g of water. This Example showed that yet another surfactant can be used according to the present invention and that a microemulsion could be prepared without KCl electrolyte.

Example 41

A polymerized microemulsion PSA was prepared from the polymerization method according to Examples 1–7 of a microemulsion of 0.89 g AA, 2.07 g AM90G Ester, 1.27 g IOA, 0.02 g of PI, 0.746 g Brij™ 96, and 0.88 g of an aqueous 4% KCl solution. This Example showed the use of another surfactant according to the present invention.

Example 42

A polymerized microemulsion PSA was prepared from the polymerization method according to Examples 1–7 of a microemulsion of 0.63 g AA, 1.46 g AM90G Ester, 0.89 g IOA, 0.02 g of PI, 0.526 g DS, and 0.62 g of an aqueous 4% KCl solution. This Example showed the use of another surfactant according to the present invention.

Example 43

A polymerized microemulsion was prepared from the polymerization method according to Examples 1–7 of a microemulsion of 1.71 g AA, 3.98 g AM90G Ester, 8.53 IOA, 0.04 of PI, 2.51 g SAM211, and 5.01 g of a 4% aqueous KCl solution. Photopolymerization was performed on a 0.38 mm thick sample on a paper release liner covered by a polyester liner according to Example 1. After polymerization, the polymerized microemulsion did not have pressure sensitive adhesive properties. However, the paper release liner was removed, and the sample was dried in a convection oven at 65° C. for 24 hours, whereupon, the sample became a polymerized microemulsion PSA of the present invention. This example demonstrated that PSA properties can be achieved from polymerized microemulsions that are not initially pressure sensitive adhesive after photopolymerization.

The polymerized microemulsion PSA was then applied to a polyurethane backing as used on Tegaderm™ brand dressings commercially available from Minnesota Mining and Manufacturing Company of St. Paul, Minn. to form a laminate. The moisture vapor transmission rate (MVTR) for the laminate of backing and adhesive was determined using a variation of ASTM Method E96-80 as described following Examples 2–7 of U.S. Pat. No. 5,270,358 (Asmus), the disclosure of which is incorporated by reference. To calculate MVTR for the adhesive according to the following equation described in Asmus, the MVTR of the laminate and the backing alone were measured.

$$1/MVTR(backing) + 1/MVTR(adhesive) = 1/MVTR(laminate)$$

The measured MVTR of the laminate was 1350, the measured MVTR of the backing was 2534, and the calculated MVTR of the polymerized microemulsion PSA of the present invention was 2889. The MVTR of the polymerized microemulsion PSA of the present invention exceeded the MVTR of the backing and demonstrated the advantages of continuous hydrophilic properties in the polymerized microemulsion PSA of the present invention.

Pressure Sensitive Adhesive Properties of Examples 1–43

Examples 1–43 were prepared again and tested according to the PSTC-1 Test Method described above. Two samples were tested for each Example to identify a "wet" adhesion state. Further two samples were placed in a vacuum oven and heated for 60 minutes at 65° C. in open face conditions: (where one of the protective liners is removed prior to placing the sample in the oven) to dehydrate the compositions of Examples 1–43 to show "dry" adhesion. The dry adhesion samples were tested after equilibration to the temperature required for the PSTC-1 Test with the top liner being immediately placed on the samples upon removal from the vacuum oven to minimize hydration prior to dry adhesion testing. The PSTC Test-1 results for both wet and dry adhesion for Examples 1–43 appear in Table 6 below.

For comparison, following the teachings of Example 10 of U.S. Pat. No. 5,238,992 (Outubuddin), a comparison microemulsion polymer blend was prepared and coated at the same thickness of 10 mils (0.254 mm) on the same type of liner having the same dimensions as used for Examples 1–43 of the present invention. Four sample strips were prepared similar to Examples 1–43. Example 10 was chosen from Outubuddin because the polymer blend possesses a Tg within a range normally expected to provide a pressure sensitive adhesive.

Significant information necessary for the preparation of Example 10 is missing and must be inferred from prior examples. The addition of AIBN and potassium persulfate is not stated in a quantity. Therefore, to prepare Example 10, the disclosure in prior Examples 1 and 2 of the amount of the addition of AIBN and the amount of potassium persulfate was used. Also, the teachings of Examples 1 and 2 were used to learn about the reaction conditions to complete the dry adhesion samples of Example 10: in both Examples 1 and 2, the polymerized sample was dried under a vacuum. Example 10 did not specify any drying. Therefore two samples of strips of Example 10 were not dried. However, because the specific time and temperature conditions were not identified in Examples 1 and 2 that provided other crucial information, the two samples of Example 10 were dried under the same conditions as used to dry the two sets of Examples 1–43: for one hour at 65° C. in a vacuum oven in open face conditions. The dry adhesion samples were tested after removal as described above.

Thus, for comparison here, the "dry" adhesion test was employed with dry adhesion samples of Example 10 of Outubuddin and dry adhesion Examples 1–43 of the present invention even though Examples 1–43 of the present invention do not require dehydration to function as polymerized microemulsion PSA's. For avoidance of doubt because the exact preparation of Example 10 is not clear, the comparison was made for both dry adhesion (a condition of a dry composition apparently favored by Outubuddin) and for wet adhesion (a condition useful in the present invention).

Table 6 shows the average value results of the two strips for both dry adhesion and for wet adhesion for Examples 1–43 in comparison with Example 10 of Outubuddin.

TABLE 6

PSTC-1 180° Peel Adhesion (newtons/100 mm)

| Example | Wet Adhesion | Wet Adhesion | Dry Adhesion | Dry Adhesion |
|---|---|---|---|---|
| 1 | 40.1 | 41.9 | 29.0 | 39.0 |
| 2 | 43.3 | 36.8 | 25.4 | 31.4 |
| 3 | 44.6 | 52.0 | 39.7 | 54.4 |
| 4 | 52.0 | 58.2 | 58.2 | 59.3 |
| 5 | 45.5 | 64.9 | 81.2 | 57.3 |
| 6 | 58.2 | 55.1 | 46.4 | 64.9 |
| 7 | 67.6 | N.A. | 85.6 | 71.4 |
| 8 | 67.6 | N.A. | 83.8 | 79.8 |
| 9 | 57.5 | N.A. | 68.9 | 58.6 |
| 10 | 29.9 | 30.6 | 36.6 | 34.1 |
| 11 | 26.3 | 27.2 | 39.9 | 34.8 |
| 12 | 23.0 | 20.3 | 31.9 | 25.2 |
| 13 | 27.4 | 25.4 | 22.7 | 32.6 |
| 14 | 20.3 | 19.6 | 29.0 | 23.2 |
| 15 | 30.1 | 35.5 | 50.0 | 31.2 |
| 16 | 54.4 | 46.2 | 65.8 | 67.1 |
| 17 | 57.1 | 61.3 | 83.4 | 85.0 |
| 18 | 35.0 | 38.1 | 51.3 | 47.1 |
| 19 | 45.9 | 47.7 | 67.8 | 69.1 |
| 20 | 32.6 | 33.9 | 78.1 | 80.1 |
| 21 | 33.7 | 41.5 | 124.2 | 125.5 |
| 22 | 128.9 | 132.5 | 165.9 | 200.5 |
| 23 | 7.8 | N.A. | 19.8 | 18.1 |
| 24 | 14.9 | 12.0 | 21.2 | 20.3 |
| 25 | 12.9 | 12.0 | 19.6 | 19.2 |
| 26 | 15.4 | 22.5 | 24.3 | 25.4 |
| 27 | 14.9 | 21.6 | 32.1 | 29.9 |
| 28 | 88.8 | 91.7 | 111.3 | 114.8 |
| 29 | 31.2 | 50.0 | 68.9 | 52.6 |
| 30 | 55.8 | 138.3 | 178.2 | 170.4 |
| 31 | 23.9 | N.A. | 27.9 | 22.1 |
| 32 | 10.3 | 10.0 | 16.9 | 20.5 |
| 33 | 65.6 | 73.8 | 88.1 | 92.1 |
| 34 | 41.0 | 36.3 | 58.4 | 71.4 |
| 35 | 8.7 | 8.3 | 56.2 | 32.8 |
| 36 | 4.0 | 4.9 | 16.5 | 19.4 |
| 37 | 12.7 | 12.9 | 17.6 | 19.0 |
| 38 | 2.7 | 3.3 | 2.2 | 2.0 |
| 39 | 2.2 | 2.9 | 1.1 | 1.3 |
| 40 | 48.6 | 52.4 | 87.9 | 83.0 |
| 41 | 72.7 | 68.2 | 101.5 | 98.1 |
| 42 | 70.5 | 64.0 | 129.8 | 134.7 |
| 43 | 17.8 | 26.5 | 75.8 | 79.4 |
| Example 10 Qutubuddin | 2.0 | 2.2 | 2.5 | 2.5 |

N.A. means not enough material was available for two tests

Table 6 shows that the wet and dry adhesion of all Examples 1–43 has an average of at least 3 Newtons/100 mm, except for Examples 38 and 39 which were observed qualitatively to be pressure sensitive adhesives immediately after formulation but did not retain pressure sensitive adhesive properties, according to the PSTC-1 Test defined for this invention above used to qualify polymerized microemulsions PSA's for the present invention. These formulations can be optimized so that polymerized microemulsions PSA's of the present invention can be made.

Table 6 also shows that some formulations are better for wet adhesion and some are better for dry adhesion.

Moreover, all but a few examples, (Examples 23, 35, 36 and 38 and 39) have wet adhesion exceeding 10 Newtons/100 mm. The wet adhesion values range from 4–132 Newtons/100 mm according to the PSTC-1 Test of the present invention.

With dry adhesion, all but Examples 38 and 39 have dry adhesion exceeding 10 Newtons/100 mm. The dry adhesion values range from 16–200 Newtons/100 mm.

With the exception of Examples 38 and 39, Examples 1–43 for both wet adhesion and dry adhesion show a wide range of acceptable 180° peel adhesion according to the PSTC-1 Test with the greater adhesiveness being more preferable. Values exceeding 15, 20, 25, 30, 40, 50, 60, 70, 80, 90, up to 200 Newtons/100 mm can be found among the samples, showing that one skilled in the art can customize adhesiveness of the polymerized microemulsion PSA's of the present invention while enjoying all of the other benefits of these novel compositions as explained above. Reference to the other tests applied to Examples 1–43 during their initial preparation shows a variety of other desirable properties for use in a variety of health care and industrial applications.

While this invention has been described in connection with specific embodiments, it should be understood that it is capable of further modification. The claims herein are intended to cover those variations which one skilled in the art would recognize as the chemical equivalent of what has been described here.

What is claimed is:

1. A mammalian skin covering comprising: an adhesive layer for contacting mammalian skin and backing layer, the adhesive layer adhered to the backing layer and comprising a polymerized microemulsion pressure sensitive adhesive composition having a continuous phase of a hydrophobic pressure sensitive adhesive polymer and a continuous phase of a hydrophilic polymer.

2. The mammalian skin covering according to claim 1, wherein the adhesive layer further comprises an antimicrobial agent.

3. The mammalian skin covering according to claim 1, wherein the backing layer comprises a film, substrate, or elastic, porous or breathable woven or nonwoven material and wherein the covering comprises a medical tape, a wound dressing, a bandage of general medicinal utility, or a medical device contacting mammalian skin.

4. A pharmaceutical delivery device comprising: an adhesive layer for contacting mammalian skin and a backing layer, the adhesive layer adhered to the backing layer and comprising a polymerized microemulsion pressure sensitive adhesive composition having a continuous phase of a hydrophobic pressure sensitive adhesive and a continuous phase of a hydrophilic polymer.

5. The pharmaceutical delivery device according to claim 4, wherein the adhesive layer further comprises a topical, transdermal, or iontophoretic therapeutic agent or pharmaceutical.

* * * * *